United States Patent
Tsai et al.

(10) Patent No.: US 11,938,156 B2
(45) Date of Patent: Mar. 26, 2024

(54) LACTIC ACID BACTERIA AND ITS APPLICATIONS

(71) Applicant: BENED BIOMEDICAL CO., LTD., Taipei (TW)

(72) Inventors: Ying-Chieh Tsai, Taipei (TW); Hui-Yu Huang, Taipei (TW); Chien-Chen Wu, Taipei (TW); Jyh-Shing Hsu, Taipei (TW)

(73) Assignee: BENED BIOMEDICAL CO., LTD., Taipei (TW)

( * ) Notice: Subject to any disclaimer, the term of this patent is extended or adjusted under 35 U.S.C. 154(b) by 252 days.

(21) Appl. No.: 16/959,891

(22) PCT Filed: Jan. 4, 2019

(86) PCT No.: PCT/CN2019/070494
§ 371 (c)(1),
(2) Date: Jul. 2, 2020

(87) PCT Pub. No.: WO2019/134690
PCT Pub. Date: Jul. 11, 2019

(65) Prior Publication Data
US 2021/0085731 A1    Mar. 25, 2021

Related U.S. Application Data

(60) Provisional application No. 62/614,296, filed on Jan. 5, 2018.

(51) Int. Cl.
| | |
|---|---|
| A61K 35/747 | (2015.01) |
| A61K 9/00 | (2006.01) |
| A61P 1/00 | (2006.01) |
| A61P 21/06 | (2006.01) |
| A61P 25/22 | (2006.01) |
| A61P 25/24 | (2006.01) |

(Continued)

(52) U.S. Cl.
CPC ......... *A61K 35/747* (2013.01); *A61K 9/0056* (2013.01); *A61P 1/00* (2018.01);
(Continued)

(58) Field of Classification Search
CPC ....... A61K 35/747; A61K 9/0056; A61P 1/00; A61P 21/06; A61P 25/00; A61P 25/24;
(Continued)

(56) References Cited

U.S. PATENT DOCUMENTS

| | | | |
|---|---|---|---|
| 9,394,575 B2 | 7/2016 | Pan et al. | |
| 2012/0020944 A1* | 1/2012 | Leser | A61P 3/10 435/252.9 |

FOREIGN PATENT DOCUMENTS

| | | | | |
|---|---|---|---|---|
| CN | 106103696 A | * | 11/2016 | A23L 33/135 |
| JP | H09002959 A | | 1/1997 | |

(Continued)

OTHER PUBLICATIONS

Cheng M.C.et al., Pharmaceutical Biology, vol. 55 No. 1, pp. 487-496, Dec. 9, 2016 (Year: 2016).*

(Continued)

*Primary Examiner* — Jana A Hines
(74) *Attorney, Agent, or Firm* — Prosyla Group, PC

(57) ABSTRACT

An isolated and purified lactic acid bacteria is provided, which is *Lactobacillus paracasei* PS23 (PS23) and its applications in delaying aging process, improving immunomodulatory activity, reducing, preventing or treating allergic and inflammation, preventing or treating a chronic disorder and/or (vi) preventing and/or treating a mood disorder or a neurological condition.

5 Claims, 22 Drawing Sheets

(51) Int. Cl.
    *A61P 25/28*     (2006.01)
    *C12N 1/20*     (2006.01)
    *C12R 1/225*     (2006.01)

(52) U.S. Cl.
    CPC ............... *A61P 21/06* (2018.01); *A61P 25/22* (2018.01); *A61P 25/24* (2018.01); *A61P 25/28* (2018.01); *C12N 1/205* (2021.05); *C12R 2001/225* (2021.05)

(58) Field of Classification Search
    CPC . A61P 25/28; A61P 37/00; C12N 1/20; C12N 1/205
    See application file for complete search history.

(56) References Cited

FOREIGN PATENT DOCUMENTS

| JP | 2015146916 A | 8/2015 |
|---|---|---|
| TW | I592487 B | 7/2017 |
| WO | 2019121666 A1 | 6/2019 |

OTHER PUBLICATIONS

Cheng M.C.et al. Prevention of hypertension-induced vascular dementia by *Lactobacillus paracasei*subsp. *paracasei* NTU 101-fermented products. Pharmaceutical Biology, vol. 55, No. 1, 487-496. Dec. 9, 2016.

Di Cerbo, Alessandro et al.: "*Lactobacillus paracasei* subsp. *paracasei* F19; a farmacogenomic and clinical update," Nutricion hospitalaria: organo oficial de la Sociedad Epanola de Nutricion Parenteral y Enteral, Nov. 1, 2013, pp. 1842-1850.

European Search Report dated Aug. 31, 2021, in EP Application No. 19736090.2.

Felis, Giovanna E et al.: "Comparative sequence analysis of a recA genefragment brings new evidence for a change in the taxonomy of the Lactobacillus casei group," International Journal of Systematic and Evolutionary Microbiology, Jan. 1, 2001, pp. 2113-2117.

Office Action issued in Japan Patent Application No. 2020-536979 dated Sep. 14, 2022. English translation included.

* cited by examiner

LACTIC ACID BACTERIA AND ITS APPLICATIONS

PRIORITY DATA

This application is a 371 National Phase of International Patent Application No. PCT/CN2019/070494, filed Jan. 4, 2019, which claims priority to and benefit of Priority Patent Application No. 62/614,296, filed Jan. 5, 2018, the contents of which are incorporated by reference in their entirety.

FIELD OF THE INVENTION

The present invention relates to a novel probiotic and its applications. In particular, the present invention relates to a new lactic acid bacteria and related compositions and methods of using it.

BACKGROUND OF THE INVENTION

The World Health Organization's (WHO) defines probiotics as "live micro-organisms which, when administered in adequate amounts, confer a health benefit on the host." It is known that probiotics such as lactic acid bacteria have an intestinal function-regulating activity, immuno-stimulating activity, and anti-cancer activity.

Various strains of lactic acid bacteria (LAB) are used in the manufacture of fermented foods, including milk, bread, vegetables, and other edible plant materials. LAB is a group of Gram-positive bacteria generally used in the production of fermented foods. The benefits of LAB in dietary and clinical applications have been widely studied. LAB have been utilized as fermenting agents for the preservation of food taking benefit of a low pH and the action of fermentation products generated during the fermentative activity thereof to inhibit the growth of spoilage bacteria. To this end, LAB have been used for preparing a variety of different foodstuff such as cheese, yogurt and other fermented dairy products from milk. It has attracted a great deal of attention in that LAB have been found to exhibit valuable properties to man and animals upon ingestion. In particular, specific strains of the genus *Lactobacillus* or *Bifidobacterium* have been found to be able to colonize the intestinal mucosa and to assist in the maintenance of the well-being of man and animal. Anti-inflammatory activity and the immunomodulatory activity are well-known characteristic of LAB. U.S. Pat. No. 7,875,421 pertains to the use of the DNA sequence of a *Lactobacillus johnsonii* strain, in particular to its genomic sequence for elucidating interactions of microorganism with hosts they colonize, and moreover for elucidating the basis of probiotic properties exhibited by such strain. WO 2018/129722 provides an isolated lactic acid bacterium (LAB), *Lactobacillus fermentum* PS150, for improving a mood disorder or a neurological condition and treating or preventing a neurodegenerative disease.

However, there is a need to develop a new probiotic beneficial to health.

SUMMARY OF THE INVENTION

The present disclosure provides an isolated and purified lactic acid bacteria, which is *Lactobacillus paracasei* PS23 (PS23), which has been deposited with Deutsche Sammlung von Mikroorganismen und Zellkulturen, DSMZ, located at Inhoffenstr. 7B, D-38124 Braunschweig, under the Budapest Treaty on Jun. 6, 2016 and was given the accession number DSMZ 32322.

The present disclosure also provides a composition comprising the PS23 cells of the invention and optionally an edible carrier or a pharmaceutically acceptable carrier. In one embodiment, the PS23 cells can be used in the form of whole bacteria which are viable cells or dead cells. In one embodiment, the composition is in the form suitable for oral administration. In a further embodiment, the composition is in the form of solid, semi-solid, liquid, granule of powder.

The present disclosure also provides use of a lactic acid bacteria of Claim 1 in the manufacture of a preparation for (i) delaying aging process (anti-aging), (ii) improving immunomodulatory activity, (iii) reducing, preventing or treating allergic, (iv) reducing, preventing or treating inflammation (v) preventing or treating a chronic disorder related to gut inflammation and/or (vi) preventing and/or treating a mood disorder or a neurological condition or treating or preventing a disease related to apoptosis of neurons or neurodegeneration in a subject. In one embodiment, the anti-aging is prevention or delay of immunosenescence, prevention or delay of sarcopenia or improvement of gut barrier or gut immune. In one embodiment, the PS23 can prevent or treat chronic disorders related to age-associated deterioration in the immune system (i.e., immunosenescence) and inflammaging. In one embodiment, the PS23 can prevent or delay sarcopenia.

In one embodiment, the disease related to apoptosis of neurons or neurodegeneration is selected from the group consisting of a stroke, Alzheimer's disease, Huntington's disease, Parkinson's disease, Pick's disease, Creutzfeldt-Jakob's disease, Parkinson-ALS-dementia complex, Wilson's disease, multiple sclerosis, progressive supranuclear palsy, neuropathic pain-related bipolar disorders, corticobasal degeneration, schizophrenia, attention deficit hyperactivity disorder (ADHD), dementia, amyotrophic lateral sclerosis, retinal disease, epilepsy, apoplexy, transient ischemic attacks, myocardial ischemia, muscle ischemia, ischemia caused by surgical techniques regarding extended suspension of blood flow to brain, a head injury, a spinal cord injury, hypoxia, and depression.

In one embodiment, the PS23 can prevent or treat stress-related disorders. In one embodiment, the PS23 can improve sleep quality and efficiency.

In one embodiment, the chronic disorder related to gut inflammation is inflammatory bowel disease or inflammatory bowel syndrome.

DETAILED DESCRIPTION OF THE INVENTION

Figure 1:
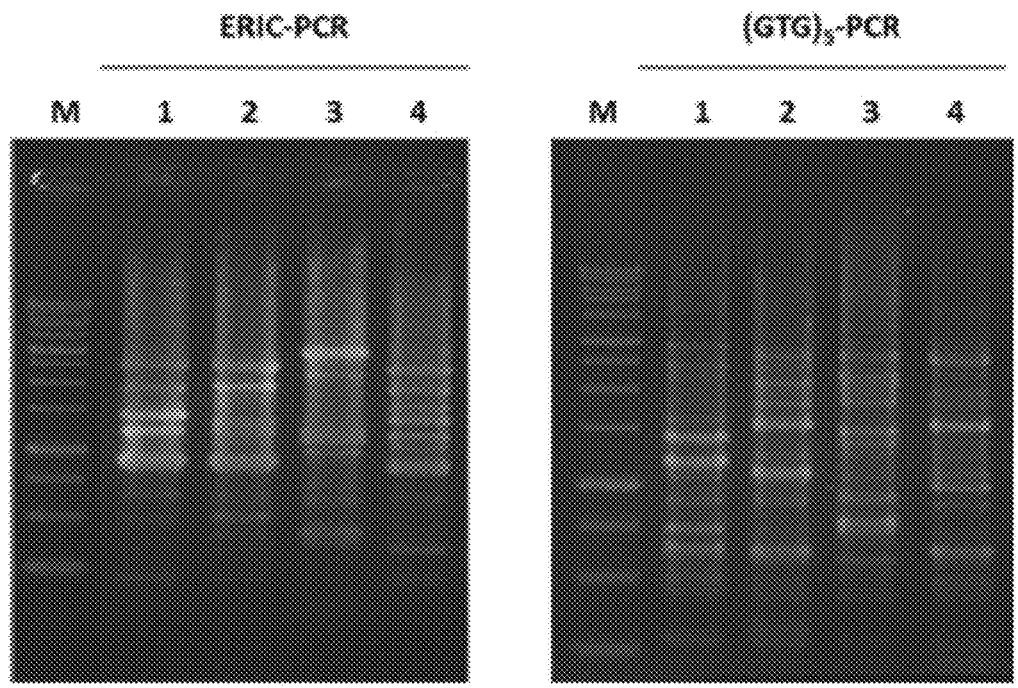
FIG. 1 shows genomic fingerprinting profile of *Lactobacillus paracasei* subsp. *Paracasei* PS23 and other *Lactobacillus casei* and *Lactobacillus paracasei* type strains. M, marker (250-10,000 bp); Lane 1, *Lactobacillus paracasei* subsp. *tolerans* ATCC 25599; Lane 2, *Lactobacillus paracasei* subsp. *paracasei* ATCC 25302; Lane 3, *Lactobacillus casei* subsp. *casei* ATCC 393; Lane 4, *Lactobacillus paracasei* subsp. *paracasei* PS23.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

As used herein, the terms "a," "an," and "the" are to be understood as meaning both singular and plural, unless explicitly stated otherwise. Thus, "a," "an," and "the" (and grammatical variations thereof where appropriate) refer to one or more.

The term "probiotic" is recognized in the state of the art as a microorganism which, when administered in adequate amounts, confers a health benefit to the host. A probiotic microorganism must fulfil several requirements related to lack of toxicity, viability, adhesion and beneficial effects. These probiotic features are strain-dependent, even among bacteria of the same species.

The term "pharmaceutically acceptable" as used herein refers to compounds, materials, compositions, and/or dosage forms which are, within the scope of sound medical judgment, suitable for use in contact with the tissues of a subject (either a human or non-human animal) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. Suitable carriers, excipients, etc. can be found in standard pharmaceutical texts.

The term "edible carrier" refers to compounds, materials, compositions, and/or dosage forms which are, suitable for use in contact with the tissues of a subject. Each carrier must also be "acceptable" in the sense of being compatible with the other ingredients of the formulation.

The term "effective amount" as used herein is the amount of colony forming units (cfu) for each strain in the composition that is high enough to significantly modify the condition to be treated in a positive way but low enough to avoid serious side effects (at a reasonable benefit/risk ratio), within the scope of sound medical judgment.

As used herein, the term "disorder" is used interchangeably with "disease" or "condition."

As used herein, the term "mood disorder" is a category of illnesses that describe a serious change in mood. Illness under mood disorder include: major depressive disorder, bipolar disorder (mania—euphoric, hyperactive, over inflated ego, unrealistic optimism), persistent depressive disorder (long lasting low grade depression), cyclothymia (a mild form of bipolar disorder), and SAD (seasonal affective disorder).

As used herein, the term "neurological condition" is a category of illnesses that describe the impact of neurological damage and disease on brain function in terms of behavior, memory or cognition. Illness under neurological condition includes but is not limited to stress (such as chronic mild stress), cognitive decline, cognitive impairment (including mild cognitive impairment (MCI)), memory lapses, general recall issues, cognitive disorders, or a neurodegenerative disease such as Alzheimer's disease, Huntington's disease, Parkinson's disease, dementia, amyotrophic lateral sclerosis, stroke, and schizophrenia.

The term "treatment" is understood as meaning to lessen or decrease at least one sign, symptom, indication, or effect of a specific disease or condition. As used herein, "prevention" is understood as to limit, reduce the rate or degree of onset, or inhibit the development of at least one sign or symptom of a disease or condition.

As used herein, the term "subject" is any animal that can benefit from the administration of a compound or composition as disclosed herein. In some embodiments, the subject is a mammal, for example, a human, a primate, a dog, a cat, a horse, a cow, a pig, a rodent, such as for example a rat or mouse. Typically, the mammal is a human.

In one embodiment, the invention provides an isolated and purified lactic acid bacteria, which is *Lactobacillus paracasei* PS23 (PS23), which has been deposited with Deutsche Sammlung von Mikroorganismen und Zellkulturen under Budapest Treaty and was given the accession number DSMZ 32322.

In one embodiment, the isolated and purified *Lactobacillus paracasei* group is isolated from healthy human faces.

In one embodiment, the 16S rRNA gene sequence and pheS gene sequence show that PS23 is highest simility to *Lactobacillus paracasei* subsp. *paracasei*.

In another aspect, the invention provides a composition comprising the PS23 cells of the invention and optionally an edible carrier or a pharmaceutically acceptable carrier. In the compositions of the invention, said PS23 cells can be used in the form of whole bacteria which may be living or not. Preferably the bacterial cells are present as living, viable cells.

The compositions of the invention can be in any form suitable for administration, in particular oral administration. This includes for instance solids, semi-solids, liquids, granules and powders.

Examples of the compositions of the invention are nutritional compositions, including food products and in particular dairy products.

The composition can be for example a capsule, tablet, drink, powder or dairy product. Optionally, other strains of probiotic (such as Lactic acid bacteria) may be present. Preferably the present nutritional composition is a baby food, an infant milk formula or an infant follow-on formula. Preferably the present composition is a nutraceutical or a pharmaceutical product, a nutritional supplement or medical food.

Nutritional compositions of the invention also include food supplements, and functional food. A "food supplement" designates a product made from compounds usually used in foodstuffs, but which is in the form of tablets, powder, capsules, portion or any other form usually not associated with aliments, and which has beneficial effects for one's health. A "functional food" is an aliment which also has beneficial effects for one's health. In particular, food supplements and functional food can have a physiological effect—protective or curative—against a disease.

If the composition according to the invention is a dietary supplement, it can be administered as such, can be mixed with a suitable drinkable liquid, such as water, yoghurt, milk or fruit juice, or can be mixed with solid or liquid food. In this context the dietary supplement can be in the form of tablets, pills, capsules, lozenges, granules, powders, suspensions, sachets, pastilles, sweets, bars, syrups and corresponding administration forms, usually in the form of a unit dose. Preferably, the dietary supplement comprising the composition of the invention is administered in the form of tablets, lozenges, capsules or powders, manufactured in conventional processes of preparing dietary supplements.

The compositions described herein can be pharmaceutically acceptable compositions, which may include one or more pharmaceutically acceptable carriers, excipients, binders, diluents or the like. The instant compositions can be formulated for various routes of administration, for example, by oral administration. They also may be provided in combination with delivery vehicles such as in some encapsulating technology.

For oral administration, powders, suspensions, granules, tablets, pills, capsules, gelcaps, and caplets are acceptable as solid dosage forms. These can be prepared, for example, by mixing one or more compounds disclosed herein with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and compositions may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

In a further aspect, the invention provides a method of (i) delaying aging process (anti-aging), (ii) improving immunomodulatory activity, (iii) reducing, preventing or treating allergic, (iv) reducing, preventing or treating inflammation (v) preventing or treating a chronic disorder related to gut inflammation and/or (vi) preventing and/or treating a mood disorder or a neurological condition or treating or preventing a disease related to apoptosis of neurons or neurodegeneration in a subject, comprising administering an effective amount of the PS23 cells of the invention or a composition containing the same to the subject. In one embodiment, the effective amount ranges from about $1 \times 10^7$ to about $1 \times 10^{13}$ cells/day of heat-killed PS23 cells or about $1 \times 10^7$ to about $1 \times 10^{13}$ CFU/day of live PS23 cells. In some embodiments, the effective amount ranges from about $1 \times 10^7$ to about $1 \times 10^{12}$, about $1 \times 10^7$ to about $1 \times 10^{10}$, about $1 \times 10^7$ to about $1 \times 10^{10}$, about $1 \times 10^8$ to about $1 \times 10^{13}$, about $1 \times 10^8$ to about $1 \times 10^{12}$ or about $1 \times 10^8$ to about $1 \times 10^{11}$ cells/day of heat-killed PS23 cells or $1 \times 10^7$ to about $1 \times 10^{12}$, about $1 \times 10^7$ to about $1 \times 10^{11}$, about $1 \times 10^7$ to about $1 \times 10^{10}$, about $1 \times 10^8$ to about $1 \times 10^{13}$ or about $1 \times 10^8$ to about $1 \times 10^{12}$ or about $1 \times 10^8$ to about $1 \times 10^{11}$ CFU/day of live PS23 cells. In a further embodiment, the effective amount is about $1 \times 10^{10}$ cells/day heat-killed PS23 cells or $1 \times 10^{10}$ CFU/day of live PS23 cells.

In one embodiment, the anti-aging includes, but is not limited to, prevention or delay of immunosenescence, prevention or delay of sarcopenia and improvement of gut barrier or gut immune.

PS23 can improve phagocytosis activity, ameliorate systemic inflammation, increase the total T cell and CD4+ cell populations, and balance the Th1/Th2 response of splenocyte. Accordingly, PS23 can prevent or treat chronic disorders related to age-associated deterioration in the immune system (i.e., immunosenescence) and inflammaging such as cardiovascular diseases, cancer and diabetes mellitus type 2.

PS23 also can prevent or delay sarcopenia. Sarcopenis is an age-related loss of muscle mass and decline in muscle strength, which is strongly associated with physical disability, poor quality of life and frailty.

In one embodiment, The diseases related to apoptosis of neurons or neurodegeneration may be selected from the group consisting of a stroke, Alzheimer's disease, Huntington's disease, Parkinson's disease, Pick's disease, Creutzfeldt-Jakob's disease, Parkinson-ALS-dementia complex, Wilson's disease, multiple sclerosis, progressive supranuclear palsy, neuropathic pain-related bipolar disorders, corticobasal degeneration, schizophrenia, attention deficit hyperactivity disorder (ADHD), dementia, amyotrophic lateral sclerosis, retinal disease, epilepsy, apoplexy, transient ischemic attacks, myocardial ischemia, muscle ischemia, ischemia caused by surgical techniques regarding extended suspension of blood flow to brain, a head injury, a spinal cord injury, hypoxia, and depression.

PS23 can increase the learning ability, memory and locomotor activities. Accordingly, PS28 can prevent and delay neurodegeneration. These effects may be achieved by reducing oxidative stress in the brain and by enhancing BDNF expression. Accordingly, PS23 can prevent or treat aging and oxidative stress related disorders in central nerve system (CNS), such as chronic brain inflammation, cerebrovascular accident, aging and neurodegenerative diseases.

In some embodiments, PS23 can prevent and treat stress-related disorders. PS23 rescues anxiety-like behavior, exploratory activity, depression-like behavior, normalize HPA axis dysfunction, increases GR and BDNF protein expression in hippocampus, and protect the neurons against stress and increases dopamine turnover rate in hippocampus.

In some embodiments, PS23 prevent and treat stress-related disorders. PS23 can rescue CORT-induced depression-like behavior, increase glucocorticoid receptor (GR), mineralocorticoid receptor (MR), and BDNF protein expression in hippocampus, protect the neurons against stress and increase serotonin level in the brain.

In some embodiments, PS23 improves sleep quality and efficiency.

In one embodiment, PS23 can improve gut permeability, reduce gut inflammation or improve mucosal immunity. In one embodiment, the chronic disorder related to gut inflammation includes, but is not limited to, inflammatory bowel disease and inflammatory bowel syndrome.

The present invention is described in greater detail by the examples presented below, which are preceded by a brief description of the figures. It goes without saying however, that these examples are given by way of illustration of the subject of the invention and do not constitute in any manner a limitation thereto.

EXAMPLES

Materials and Methods 1.1. Preparation of PS23

PS23 (DSM 32322) was isolated from healthy human feces. It was identified as a novel strain by phylogenetic classification of its 16S rDNA sequence. The isolated PS23 was inoculated in Man Rogosa Sharpe broth (MRS; BD Difco, Becton-Dickinson, Sparks, MD MD, USA), cultured at 37° C. for 18 h, and then harvested by centrifugation at 6000×g for 10 min. The pellet was re-suspended in MRS plus 12.5% glycerol to a final concentration of $5 \times 10^9$ colony-forming units per milliliter. The re-suspended solution was then aliquoted in freezer tubes and stored at −20° C. until use. When in use the aliquot was pre-warmed to 37° C. for 1 h and re-suspended in saline before being administered to mice.

1.2. Animals and Housing

All mice used in this study were purchased from the National Laboratory Animal Center (NLAC; Taipei, Taiwan) and accommodated in the animal center at National Yang-Ming University. The room was kept at 22±2° C., 50-60% humidity, and under 12 h light/dark cycle. Unless otherwise stated, the mice were provided with water and chow ad libitum (Lab Diet Autoclavable Rodent Diet 5010; PMI Nutrition International, Brentwood, MO, USA). All animal experimental procedures were reviewed and approved by the Institutional Animal Care and Use Committee, National Yang-Ming University. Mice were acclimated for one week before the experiments were started.

1.3. Experimental Design and Sample Collection

For the DSS-induced UC mouse model, female BALB/c mice (6-8 week sold) were random assigned to health (CON), UC control (DSS), DSS+heat-killed PS23 (Heat-killed), and DSS+live PS23 (Live) groups. From day 1 to 7, CON and DSS groups were both orally administered saline; while the Heat-killed and Live groups were orally administered with heat-killed ($1\times10^9$ cells/mouse/day) or live PS23 ($1\times10^9$ CFU/mouse/day), respectively. On day 8, drinking water of all DSS groups were replaced with 5% DSS water (g/mL). On day 14, feces of the mice were collected for measuring fecal occult blood level. After collected feces, mice were sacrificed using $CO_2$ asphyxiation. The colon was carefully excised for measurement of the length from the caecum to the anus. Then a small part of distal colon was cut immediately after the measurement and fixed in 10% phosphate-buffered formalin for histology use. The rest part of the colon was stored at $-80°$ C. until colonic protein extraction.

For the MS mouse model, timed-pregnant female C57BL/6J mice were used. To evaluate the psychotropic effects of PS23, we administered PS23 to the MS experimental group. The MS groups were given saline re-suspended heat-killed ($1\times10^9$ cells/mouse/day) or live PS23 ($1\times10^9$ CFU/mouse/day) by gavage for 4 weeks from PD29, whereas the MS and naïve control groups were given saline during the same period. At the end of the PS23 treatment period, the mice underwent a battery of behavioral tests. The tests were given in sequence from the least stressful to the most stressful in the following order: open field test (OFT); elevated plus maze (EPM); and forced swimming test (FST). All the tests were conducted during the light phase.

1.4 Prepared of Colon Tissue Homogeneous Supernatant

Colon tissue was homogenized in RIPA lysis buffer (50 mM Tris-HCl, pH 7.5, 150 mM NaCl, 0.5% sodium deoxycholate, 1% NP-40, and 0.1% SDS) in the presence of protease inhibitors (Sigma-Aldrich, St. Louis, MO). Colonic protein homogenates were incubated for 15 min on ice and then centrifuged at 12,000 g for 10 min at $4°$ C. The supernatants were collected and stored at $-80°$ C. until analysis. Protein contents were determined using the Bradford assay.

1.5 Determined of Cytokine Production

The level of cytokines in serum or colon tissue homogeneous supernatant were measurement by commercial kit (IFN-$\gamma$ and IL-10 used by Biolegand ELISA kit; IL-8, TNF-$\alpha$, IL-1p and IL-6 used by eBioscience ELISA kit).

1.6 Myeloperoxidase Activity Assay

The level of colon tissue homogeneous supernatant myeloperoxidase (MPO) activity was measurement by commercial kit which is Cayman MPO peroxidation assay kit.

1.7 Open Field Test

Locomotor activity of the mice was examined by the OFT. In this test the mouse was placed in the open field activity chamber for 10 min (Tru Scan Activity System; Coulbourn Instruments, Whitehall, PA, USA). The square activity chamber (25.4×25.4×38 cm) is made of Plexiglas walls with two photobeam sensor bars on each side. The box was cleaned with 70% ethanol after each test. The activities were automatically recorded and quantified with the Tru Scan 2.2 software (Coulbourn Instruments). The total distance traveled, moving time, and center distance and time were measured by the Tru Scan Activity System. The center area was defined as a region in the center measuring 12.5×12.5 cm.

1.8 Elevated Plus Maze Test

The elevated plus maze is composed of two closed arms and two open arms (height, 45 cm; full arm length, 66 cm; arm width, 10 cm; wall height of closed arm, 30 cm). This test was used to assess anxiety-like behavior of the mice. The mouse was placed in the center arm crossing area (10×10 cm) and allowed free exploration in the maze for 10 min. The maze was cleaned with 70% ethanol after each test. The mouse activity was recorded by a video camera mounted on the ceiling of the maze center. The recorded activity was later analyzed by EthoVision video tracking software (Noldus Information Technology, Wageningen, the Netherlands). The total travel distance and duration spent in the open and closed arms were quantified.

1.9 Forced Swimming Test

The FST was used to assess the depression-like behaviors in the mice. Briefly, mice were put in a transparent acrylic cylinder (height, 30 cm; internal diameter, 10 cm) containing 15 cm water (23-25° C.) to swim for 6 min on the first day. After the swim, the mice were dried with tissue paper and returned to their home cage. The next day, the mice were given a second swim session for 5 min. The swim sessions were recorded by a video camera and the behavior was analyzed by EthoVision video tracking software. The immobility time during the second session was quantified.

1.10 Serum Corticosterone

The serum was diluted first, and then we used a commercial CORT EIA kit (Cayman Chemical, Michigan, MI, USA) to analyze corticosterone concentration. The corticosterone concentration was interpolated using the standards provided in the kit following the manufacturer's instructions.

1.11 Statistical Analysis

All data were expressed as mean±SEM or mean±SD. Differences between groups were analyzed by one-way or two-way analysis of variance (ANOVA) with Bonferroni's post-test or two-tailed t-test when appropriate.

Example 1 Genetic Typing of *Lactobacillus paracasei* PS23

The following table lists those organisms, whose 16S rRNA and pheS DNA sequences show the highest similarity values compared to the 16S rRNA sequence and pheS DNA sequence of PS23.

| % 16s rRNA gene sequence identity of strain P523 | |
|---|---|
| Lactobacillus paracasel subsp. paracasel NCDO 151$^T$ | 100.00 |
| Lactobacillus paracasel subsp. tolerans NBRC 15906$^T$ | 99.93 |
| Lactobacillus case; subsp. casei ATCC 393$^T$ | 99.21 |
| Lactobacillus rhamnosus ATCC 7469$^T$ | 98.87 |
| E. coil J01695 | 77.82 |

| % pheS gene Sequence identity of strain P523 | |
|---|---|
| Lactobacillus par acasef subsp. paracasef LMG 13087$^T$ | 99.75 |
| Lactobacillus paracasel subsp. tolerans LMG 9191$^T$ | 99.49 |
| Lactobacillus casei LMG 6904$^T$ | 82.16 |
| Lactobacillus rhamnosus LMG6400$^T$ | 80.56 |
| Leuconostoc factis LMG 88941 | 65.66 |

The comparison of 16S rRNA gene and pheS gene indicates that PS23 belongs to *Lactobacillus paracasei* subsp. *paracasei*.

The genomic fingerprinting analyzed by ERIC-PCR and $(GTG)_5$-PCR shows that PS23 is a novel strain of *Lactobacillus paracasei* (see FIG. 1).

Sugar utilization of PS23 was investigated using API 50 CHL kit (bioMerieux, France). The fermentation test indicates that PS23 harbors a biochemical property similar to *Lactobacillus paracasei* subsp. *paracasei*.

| Carbohydrates substrate | PS23 (DSM 32322) |
|---|---|
| CONTROL | − |
| Glycerol | + |
| Erythritol | − |
| D-Arabinose | − |
| L-Arabinose | − |
| D-Rtbose | + |
| D-Xylose | − |
| L-Xylose | − |
| D-Adonitol | − |
| Methyl-β-D-Xylopyranoside | − |
| D-Galactose | + |
| D-Glucose | + |
| D-Fructose | + |
| D-Mannose | + |
| L-Sorbose | + |
| L-Rhomnose | − |
| Dulcitol | − |
| Inositol | + |
| D-Ma,nnitol | + |
| D-Sorbitol | + |
| Methyl-α-D-mannopyranoside | − |
| Metityl-α-D-glucopyranoside | + |
| N-Acetyl glucosamine Amygdalin | + |
| Arbutin | + |
| Escultn ferric citrate | + |
| Salicin | + |
| D-Cellobiose | + |
| D-Mattose | + |
| D-Lactose (bovine origin) | + |
| D-Melibiose | − |
| D-Saccharose (sucrose) | + |
| D-Trehatose | + |
| Inulin | + |
| D-Melezitose | + |
| D-Raffinose | − |
| Amidon (starch) | − |
| Glycogen | − |
| Xylitol | − |
| Gentiobiose | + |
| D-Turanose | + |
| D-Lyitose | + |
| D-Tagatose | + |
| D-Fucose | − |
| L-Fucose | − |
| D-Arabitol | − |
| L-Arabitol | + |
| Potassium gluconate | + |
| Potassium 2-ketogluconate | ± |
| Potassium S-ketogluconate | − |

+, positive; −, negative; ±, weak

Example 2: PS23 Reduced Gut Bleeding

Figure 2:
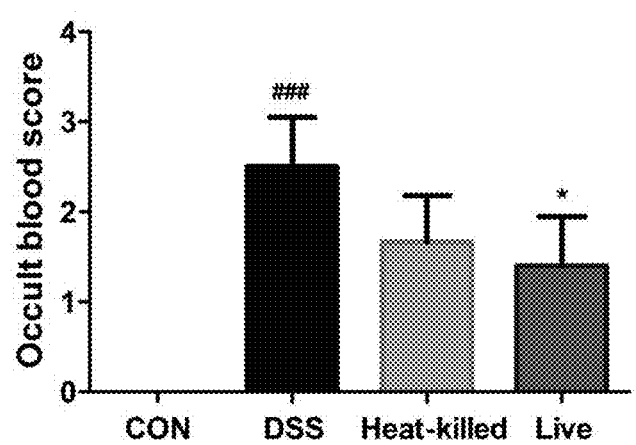
FIG. 2 shows the reduction of occult blood score of feces by heat-killed or live PS23.

Since 5% DSS daily for 7 days could cause severe tissue damage and results in bleeding in the gut, there might be blood in the feces in the DSS treated groups. To measure the severity of the gut inflammation, we collected feces from each mouse for occult blood analysis on day 13. Sample with darker color was scored higher. As shown in FIG. 2, fecal occult blood score was significantly higher in the DSS group than the control group ($p<0.0001$), indicating the increased gut bleeding after DSS challenge. This was supported by our observation that the feces and their anus were bloody, indicating that all DSS-treated mice were suffering from minor to severe gut inflammation. Chronic administration of heat-killed or live PS23 was able to reduce the bleeding because the fecal occult blood scores were found lower (FIG. 2). Live PS23 in particularly, reduced the bleeding more effectively than its heat-killed form, as the score was significantly lower than the DSS group (FIG. 2; $p<0.05$).

Example 3 PS23 Reduced DSS-Induced Colon Shortening

Figure 3:
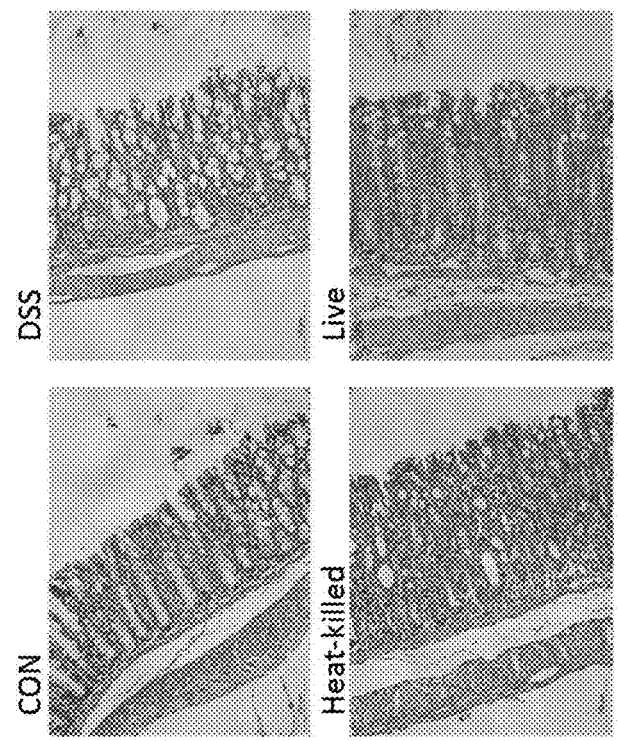
FIGS. 3 A and B show the reduction of DSS-induced colon shortening by PS23. A, The average length in the DSS-treated group is significantly shorter than control group. B, PS23 rescues the DSS-induced tissue damage in the colon.
Figure 3:
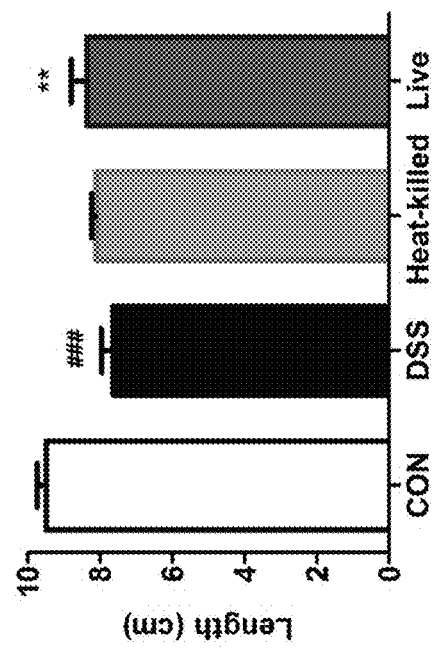

Shortened colon length is featured in the DSS murine model. We found that the average length in the DSS-treated group was significantly shorter than control group (FIG. 3A; $p<0.0001$). However, the length was longer in PS23 groups, especially in the Live group that was significantly longer than the DSS group (FIG. 3A; $p<0.01$). In addition, we found that there was more concrete stool in the colon of the mice in the Live PS23 group, indicating a reduced diarrhea by the administration. Furthermore, histology showed that PS23 rescued the DSS-induced tissue damage in the colon (FIG. 3B), as evaluated according to observations on enterocyte loss, crypt inflammation, neutrophils, lamina propria, epithelial hyperplasia, and mononuclear cells.

Figure 4:
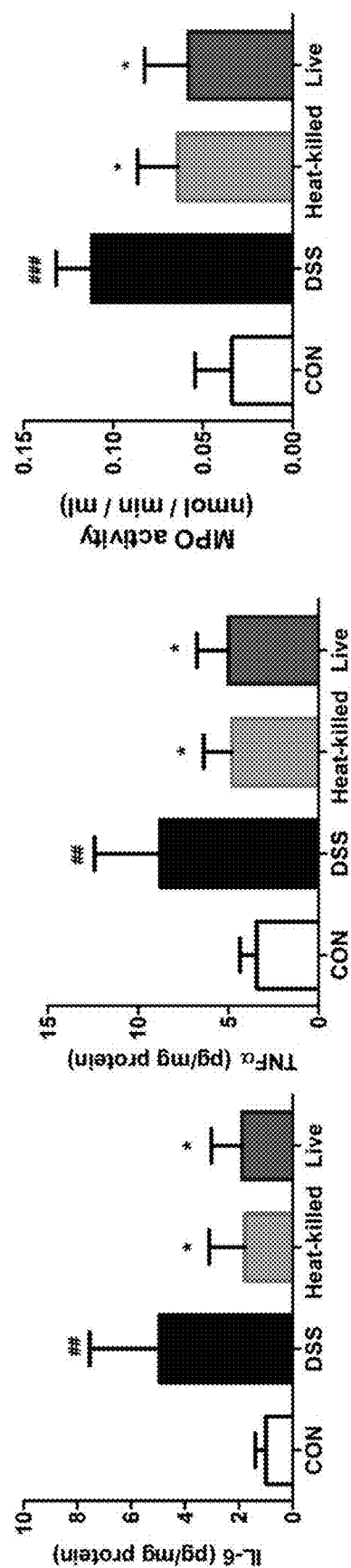
FIG. 4 shows that PS23 reduces colonic pro-inflammatory cytokine levels and MPO activity.

Example 4 PS23 Reduced Colonic Pro-Inflammatory Cytokine Levels and MPO Activity DSS-induced gut inflammation and increases of TNF-alpha, IL-6, and MPO activity in colonic tissue have been reported in the DSS-colitis model. We found similar results as TNF-alpha, IL-6, and MPO activity in the colon tissue of DSS-treated mice were increased (FIG. 4). On the other hand, administration of both heat-killed and live PS23 reduced all the cytokine levels and MPO activity in the colon tissue, while reductions on TNF-alpha, IL-6, and MPO activity in both groups reached significant difference statistically to the DSS group (FIG. 4; $p<0.05$).

Figure 5:
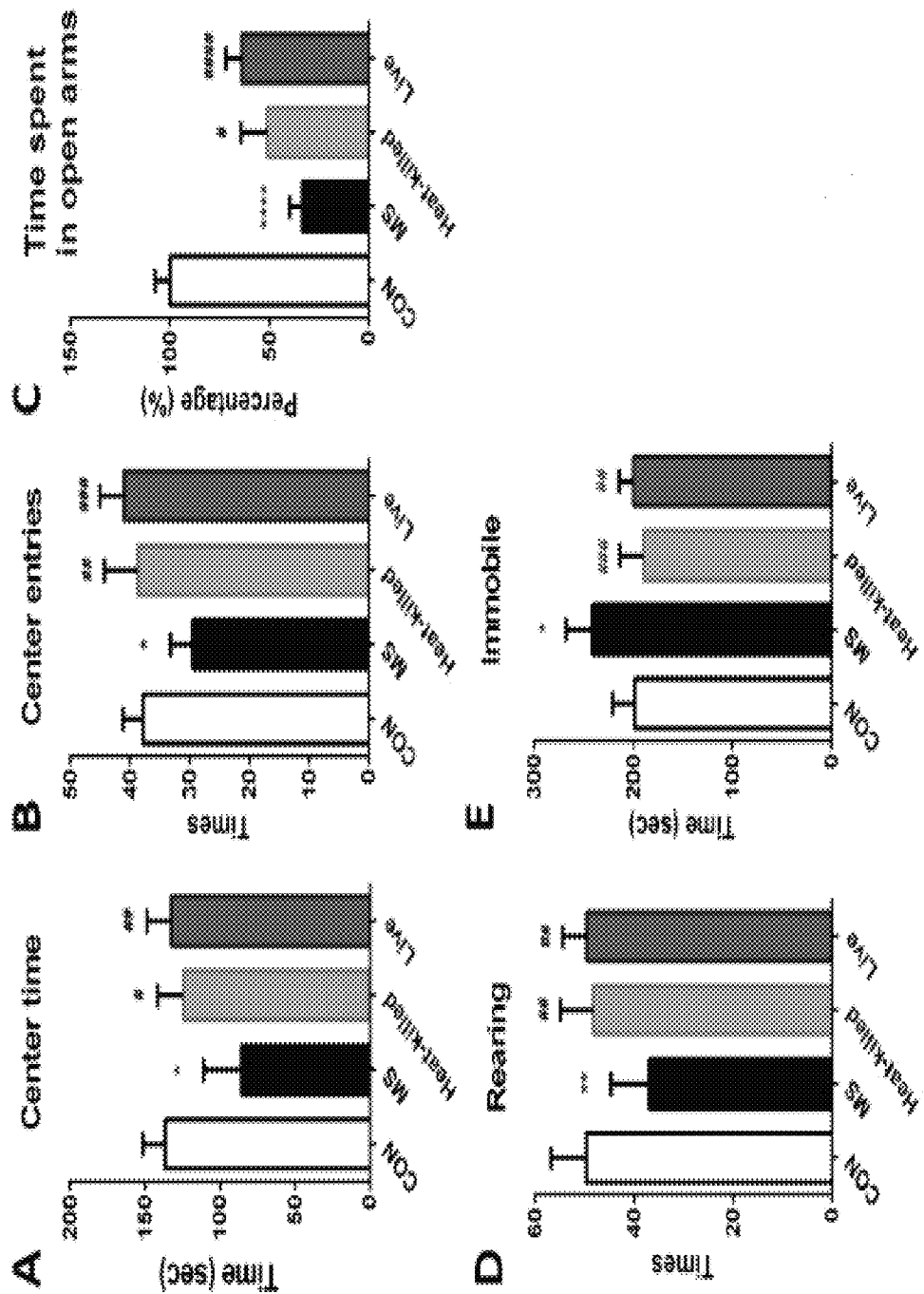
FIG. 5 A to E show that PS23 is able to reverse abnormal phenotypes induced by early life stress. A and B, The time spent and the entries into central region of the open field arena in MS mice are reduced. C, The percent time spent in the open arms of the EPM in MS mice is reduced. D, The rearing frequency is reduced, indicating that the MS mice have reduced exploratory activity. E, MS not only produces mice with anxiety-like behavior, but also produces mice with depression-like behavior.

Example 5 PS23 Rescued MS-Induced Anxiety-Like Behavior and Exploratory Activity We applied MS to C57BL/6J mice and used open field test (OFT), elevated plus maze (EPM), and forced swimming test (FST) to assess behaviors of the MS mice. As shown in FIG. 5, the time spent and the entries into central region of the open field arena were reduced (FIGS. 5A and 5B), as well as the percent time spent in the open arms of the EPM was reduced (FIG. 5C), indicating that MS caused mice more anxious. In addition, we also found the rearing frequency was reduced (FIG. 5D), indicating that the MS mice have reduced exploratory activity. Furthermore, we found MS not only produced mice with anxiety-like behavior, but also produced mice with depression-like behavior, as in the FST the immobile time was increased (FIG. 5E). Interestingly, administration of both heat-killed and live PS23 for 4 weeks rescued these reductions (FIG. 5A-5E), indicating that PS23 was able to reverse abnormal phenotypes induced by early life stress.

Example 6 PS23 Normalized MS-Induced Inflammation

Figure 6:
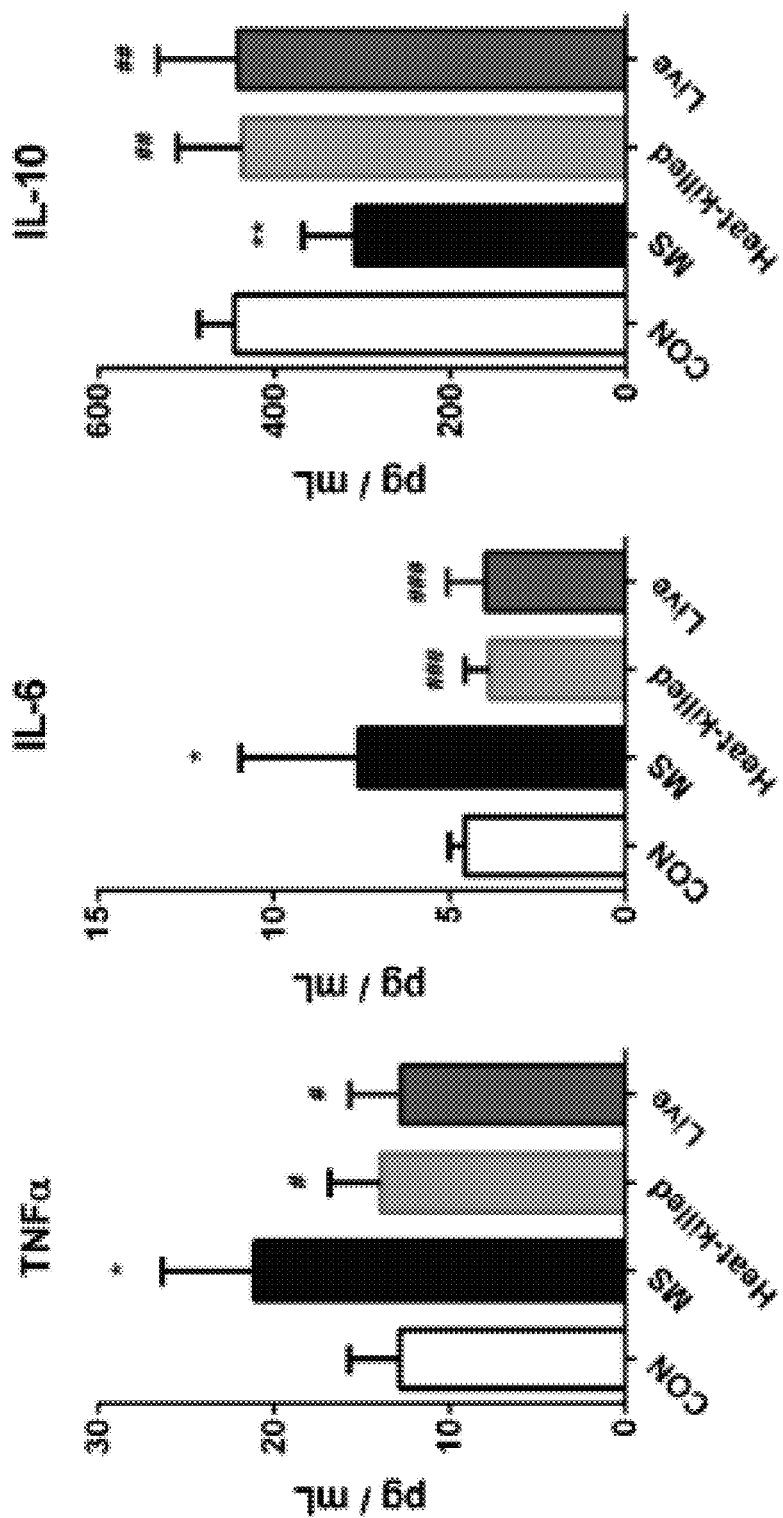
FIG. 6 shows that PS23 normalizes MS-induced inflammation.

We found that MS shifted the immunity of the mice toward increased inflammation, as serum TNF-alpha and IL-6 were higher in the MS group, whereas the anti-inflammatory cytokine, IL-10, was lower than control (FIG. 6). On the other hand, we found chronic administration of PS23 reduced the inflammation shown by the decreased serum TNF-alpha and IL-6, and increased IL-10 level (FIG. 6). Since over activated immune response increases the risk of getting physical and psychological dysfunctions, our findings in the MS mice may echoed the anti-inflammatory effect of PS23 shown in the previous DSS experiment and might partially underlie how PS23 ameliorated the anxiety- and depression-like behavior of the MS mice.

Example 7 PS23 Normalized MS-Induced HPA Axis Dysfunction

Figure 7:
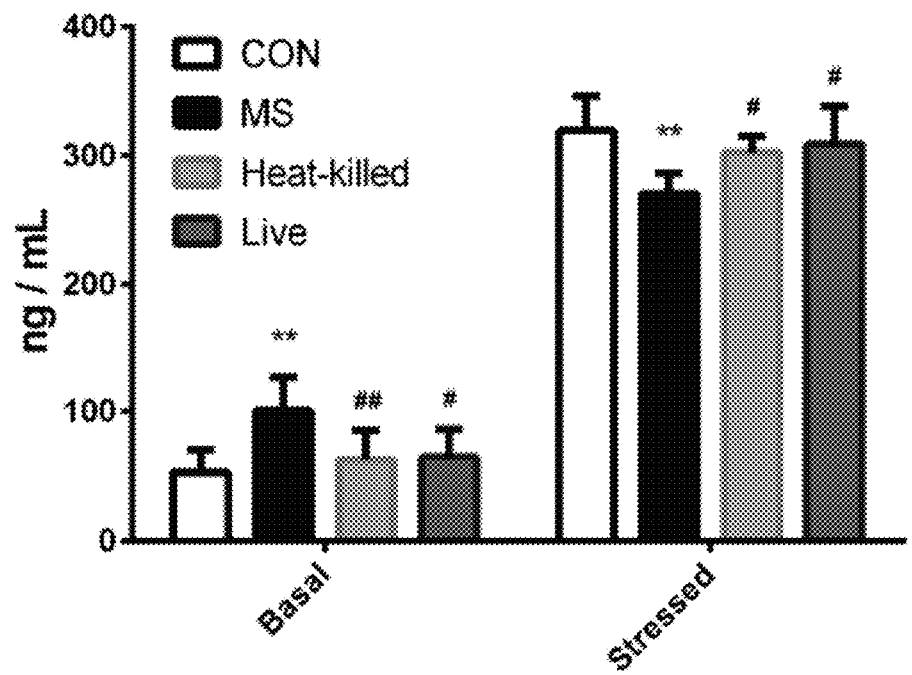
FIG. 7 shows that PS23 normalizes MS-induced HPA axis dysfunction.

In agreement with most of the previous studies show that MS disrupt HPA axis, we found the CORT levels were different at both basal and stressed states when compared to the non-MS control mice, and the HPA axis activity was hyperactivated at basal state (FIG. 7; p<0.01). Nonetheless, we found that a blunt CORT level 30 min after FST, and the ratio of stressed to basal CORT level was significantly lower than control (FIG. 7; p<0.0001), suggesting that the HPA axis was impaired by MS and was unable to maintain a sufficient CORT level upon stimuli. In contrast, CORT levels in both heat-killed and live PS23 were rescued from the MS group to nearly control levels (FIG. 7), indicating that PS23 was able to normalize the dysregulated HPA axis.

Example 8 PS23 Increased GR and BDNF Protein Expression in Hippocampus

Figure 8:
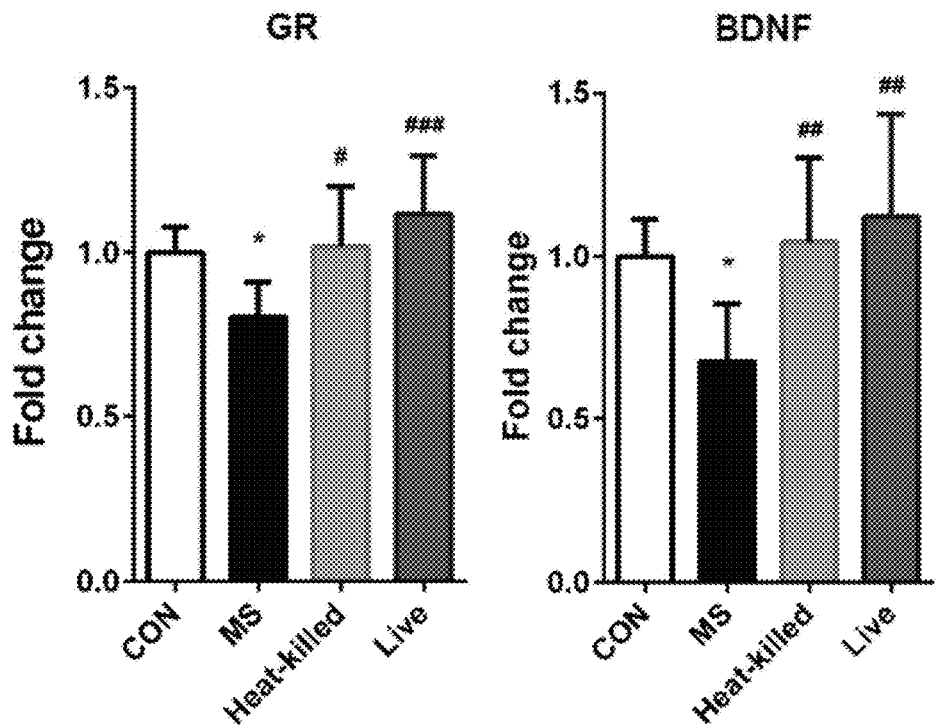
FIG. 8 shows that PS23 increases GR and BDNF protein expression in hippocampus.

GR is the main receptor responsible for feedback inhibition in HPA axis. To investigate the effect of MS and PS23 on the HPA axis in more detail, we examined hippocampal GR protein levels. We found the GR expression was reduced in MS mice (FIG. 8), indicating that MS impaired the feedback loop of the HPA axis that may be responsible for the elevated serum CORT level in the MS group. In addition, we found that BDNF protein level was reduced in this region (FIG. 8). Alteration of BDNF level in the hippocampus is associated with depression. It is possible that during early life, MS procedure impairs hippocampal development in mice and results in insufficient level of BDNF that both weakened stress response. On the contrary, chronic administration of both heat-killed and live PS23 was able to reverse the reduced protein level of GR and BDNF as the levels were significantly increased compared to MS group (FIG. 8; p<0.05), and protect the hippocampal neurons against stress.

Figure 9:
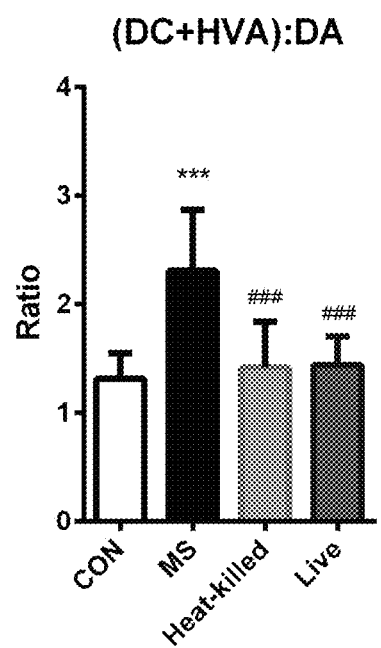
FIG. 9 shows the turnover rate of dopamine in the hippocampus of maternal separation mice. Data are presented as mean±SD. ***$p<0.001$ versus CON group; ###$p<0.001$ versus MS the group.

Oral administration of live or heat-killed PS23 increased dopamine turnover rate in hippocampus (FIG. 9).

Figure 33:
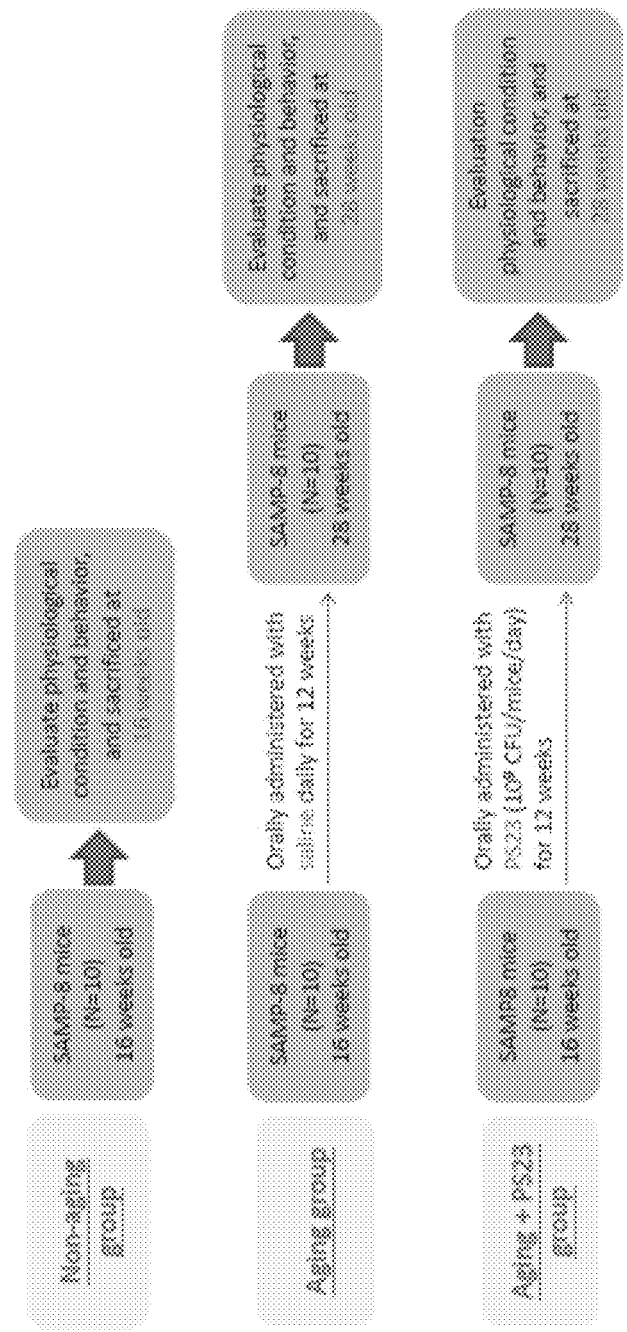
FIG. 33 shows an experimental design.

Example 9 Anti-Aging Study in Senescence Accelerated Mouse-Prone 8 (SAMP8) Mice Model The experimental design is shown in FIG. 33.

Figure 10:
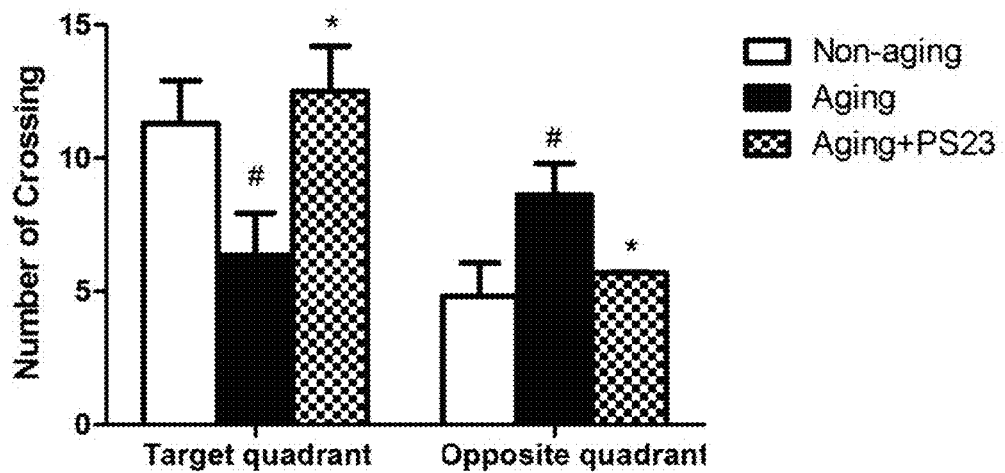
FIG. 10 shows the behavioral assessment for learning and memory in SAMP8 mice by Morris water maze test. Data are presented as mean+/−SD. #$p<0.05$ versus non-aging group; *$p<0.05$ versus aging group.

PS23 prevented and delayed neurodegeneration. Oral administration of PS23 increases the learning and memory ability in aged SAMP8 mice (FIG. 10).

Figure 11:
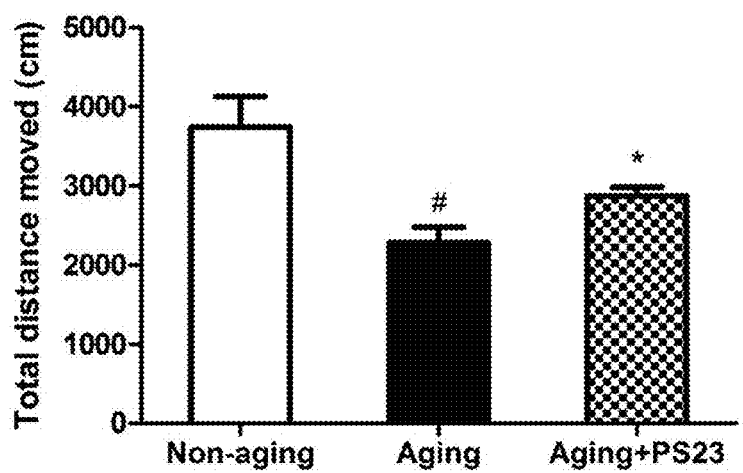
FIG. 11 shows that locomotor activity of SAMP8 mice is assessed by open field test. Data are presented as mean+/−SD. #$p<0.05$ versus non-aging group; *$p<0.05$ versus aging group.

Oral administration of PS23 increased the locomotor activities in aged SAMP8 mice (FIG. 11).

Figure 12:
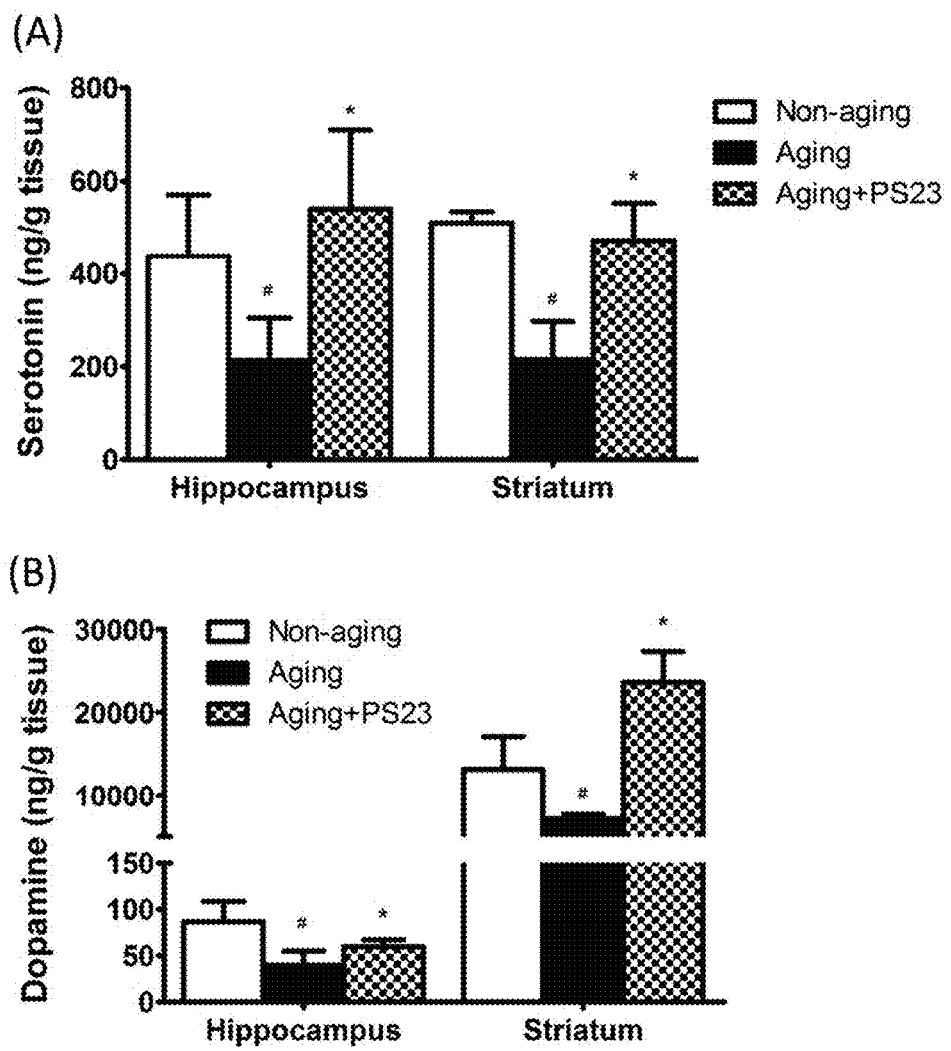
FIGS. 12 A and B show the serotonin (A) and dopamine (B) level in the brain tissue of SAMP8 mice. Data are presented as mean±SD. #$p<0.05$ versus Non-aging group; *$p<0.05$ versus Aging group.

Oral administration of PS23 increased the neurotransmitter level such as serotonin and dopamine in aged SAMP8 mice (FIGS. 12 (A) and (B)).

Figure 13:
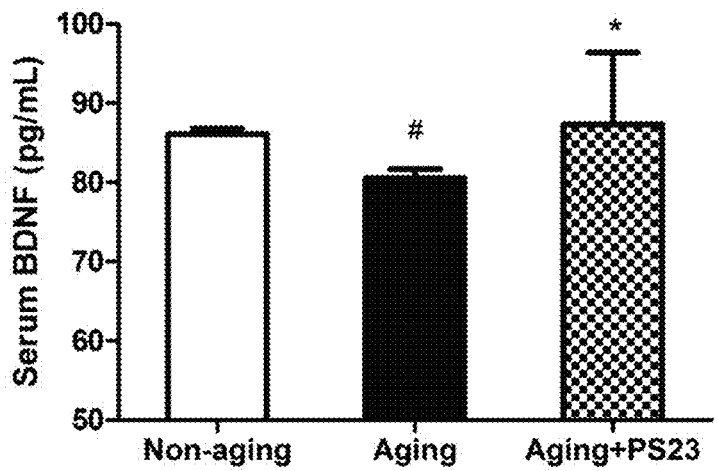
FIG. 13 shows the level of serum BDNF in SAMP8 mice. Data are presented as mean+/−SD. #$p<0.05$ versus non-aging group; *$p<0.05$ versus aging group.

Oral administration of PS23 increased the level of serum BDNF in aged SAMP8 mice (FIG. 13).

Figure 14:
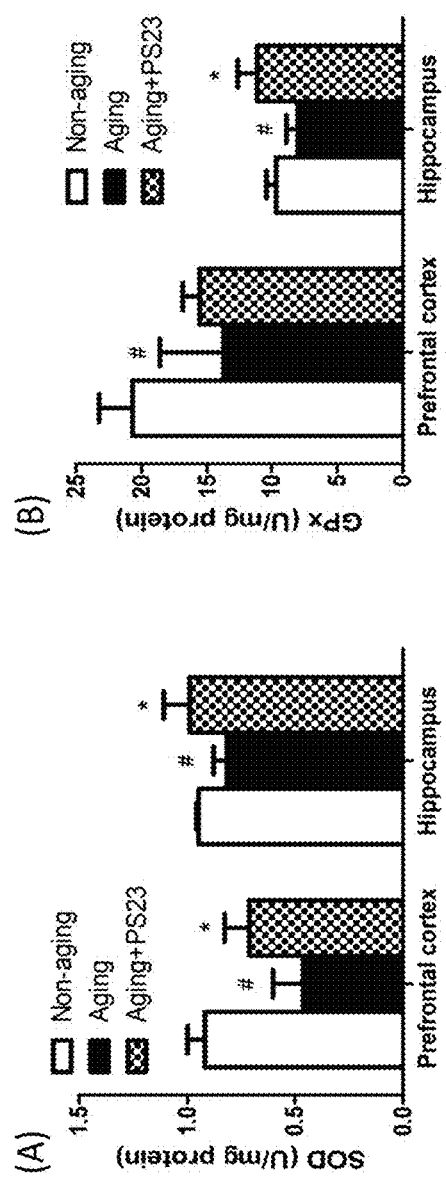
FIGS. 14 (A) and (B) show the level of SOD (A) and the level of glutathione peroxidase (GPx) (B) in prefrontal cortex and hippocampus in SAMP8 mice. Data are presented as mean±SD. #$p<0.05$ versus Non-aging group; *$p<0.05$ versus Aging group.

Oral administration of PS23 increased the level of anti-oxidant enzyme such as superoxide dismutase (SOD) and glutathione peroxidase (GPx) in prefrontal cortex and hippocampus of aged SAMP8 mice (FIGS. 14 (A) and (B)).

Figure 15:
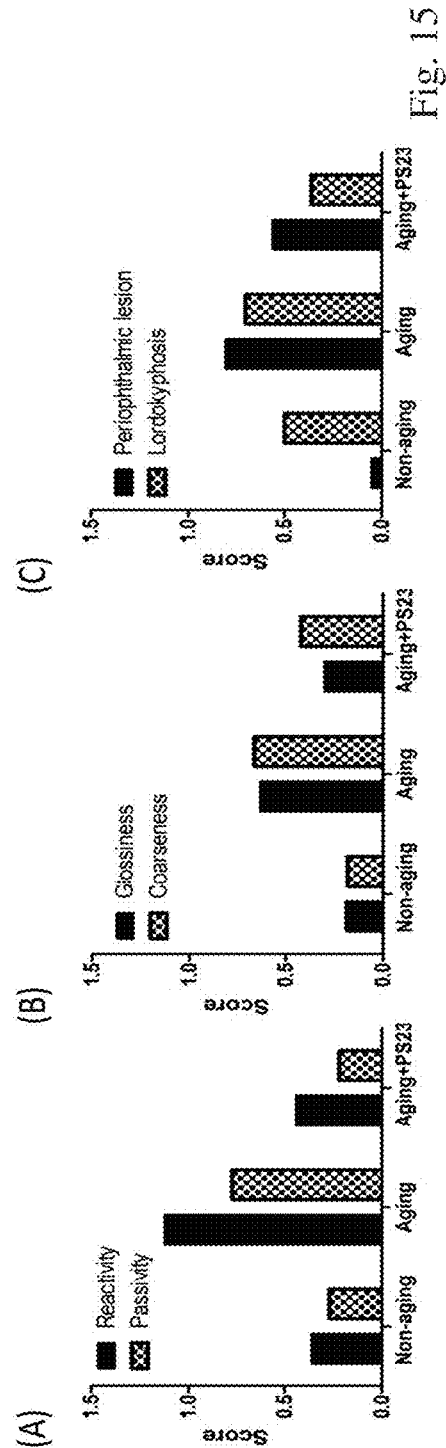
FIGS. 15 (A) to (C) show the evaluation of the degree of senescence of SAMP8 mice. The evaluation categories include behavior (A), skin and hair (B), and eyes and spine (C). Data are presented as mean+/−SD. The grading score system were followed Takeda et al., 1981 (Mech Ageing Dev. 1981, 17(2):183-94).

Oral administration of PS23 delayed and prevented aging related physiological changes in aged SAMP8 mice (FIGS. 15, (A) to (C)).

Figure 16:
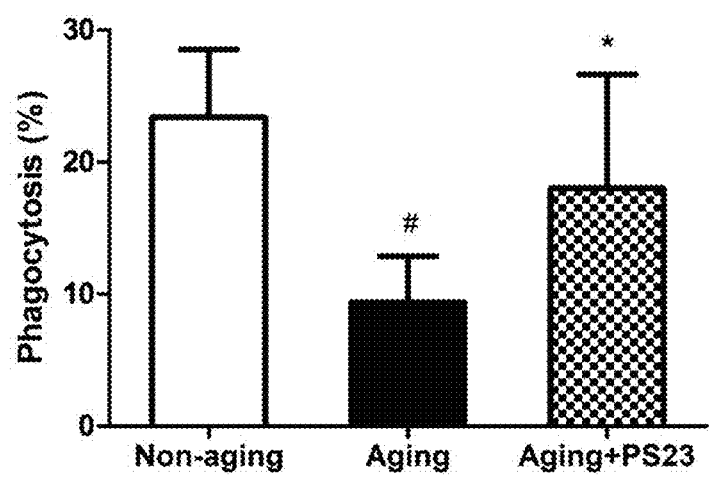
FIG. 16 shows phagocytosis activity of SAMP8 mice. Data are presented as mean+/−SD. #$p<0.05$ versus non-aging group; *$p<0.05$ versus aging group.

Oral administration of PS23 improved phagocytosis activity impaired by aging in aged SAMP8 mice (FIG. 16).

Figure 17:
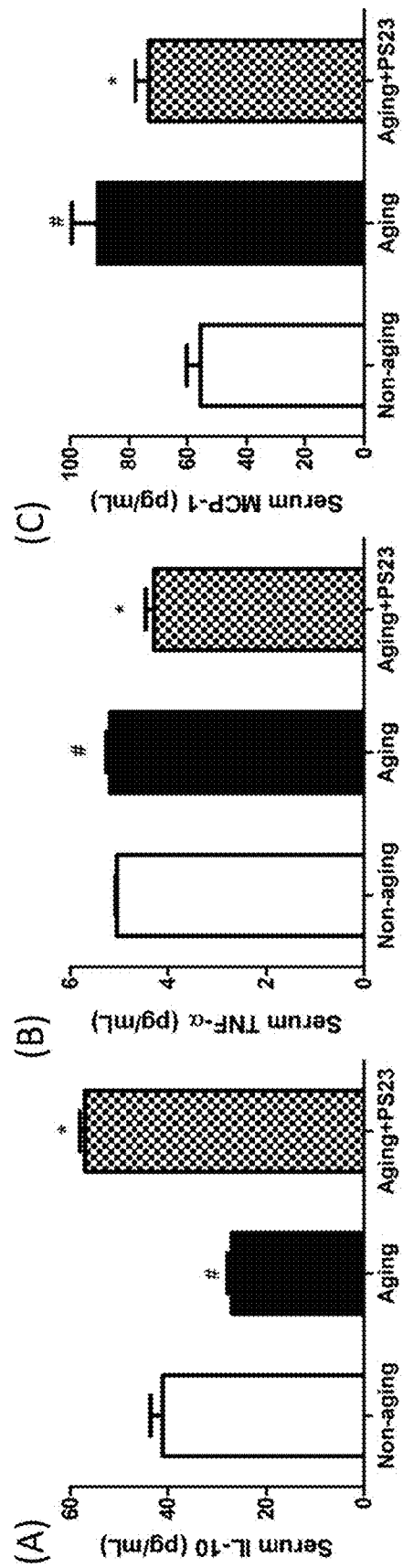
FIGS. 17 (A) to (C) show the levels of serum IL-10 (A), TNF-alpha (B) and MCP-1 (C) in SAMP8 mice. Data are presented as mean+/−SD. #$p<0.05$ versus non-aging group; *$p<0.05$ versus aging group.

Oral administration of PS23 ameliorated systemic inflammation by increasing anti-inflammatory cytokine IL-10, decreasing pro-inflammatory cytokine TNF-alpha, and decreasing inflammatory chemokine MCP-1 in aged SAMP8 mice (FIGS. 17 (A) to (C)).

Figure 18:
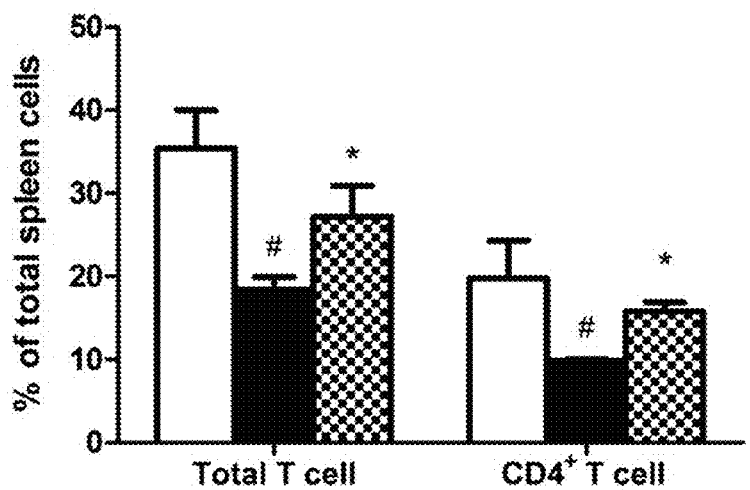
FIG. 18 shows the percentage of total T cell and CD4+ cell in spleen cells in SAMP8 mice. Data are presented as mean+/−SD. #$p<0.05$ versus non-aging group; *$p<0.05$ versus aging group.

Oral administration of PS23 increased the total T cell and CD4+ cell populations in spleen cells in aged SAMP8 mice (FIG. 18).

Figure 19:
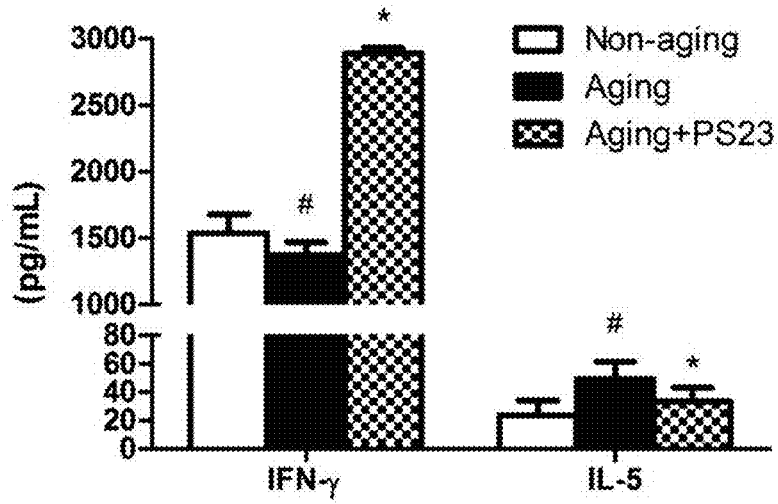
FIG. 19 shows the level of IFN-gamma and IL-5 produced by ConA stimulated SAMP8 splenocytes. Data are presented as mean+/−SD. #$p<0.05$ versus non-aging group; *$p<0.05$ versus aging group.

Oral administration of PS23 increased the IFN-gamma production and decreased the IL-5 of aged SAMP8 mice splenocytes stimulated by CoA (FIG. 19).

Figure 20:
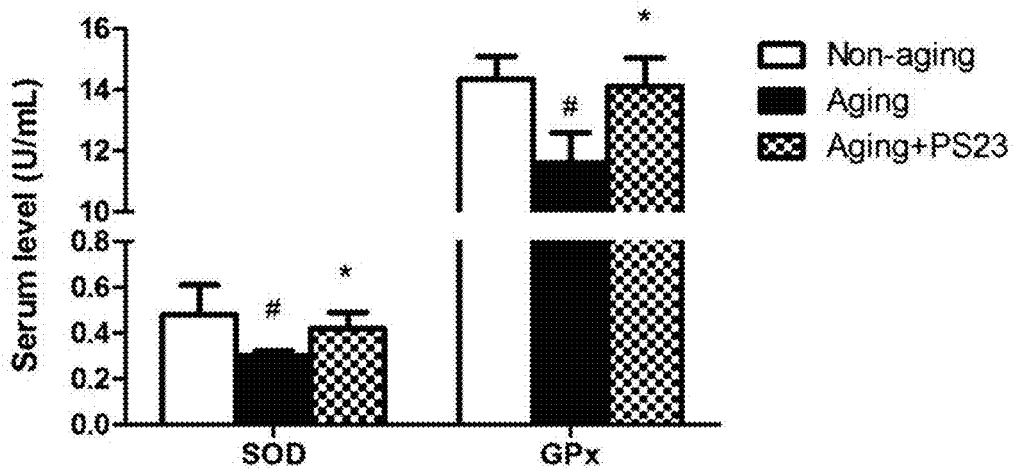
FIG. 20 shows the effects of PS23 on the serum level of SOD and GPx in SAMP8 mice. Data are presented as mean+/−SD. #$p<0.05$ versus non-aging group; *$p<0.05$ versus aging group.

Oral administration of PS23 increased the level of anti-oxidant enzymes such as superoxide dismutase (SOD) and glutathione peroxidase (GPx) in the serum of aged SAMP8 mice (FIG. 20).

Figure 21:
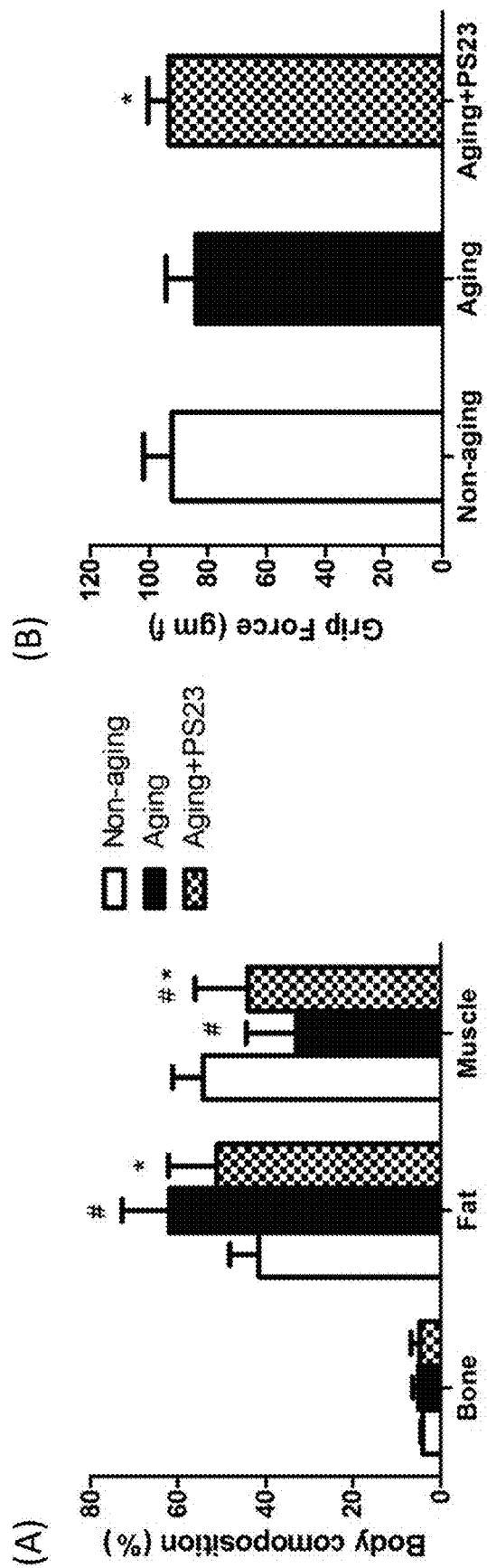
FIGS. 21 (A) and (B) show the body composition (A) and forelimb grip strength (B) of SAMP8 mice. Data are presented as mean+/−SD. #$p<0.05$ versus non-aging group; *$p<0.05$ versus aging group.

Oral administration of PS23 increased the muscle mass and griped strength of aged SAMP8 mice (FIGS. 21 (A) and (B)).

Figure 22:
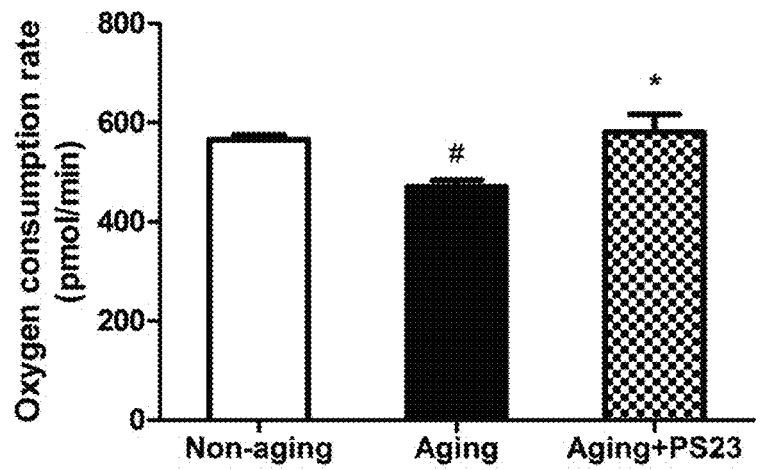
FIG. 22 shows oxygen consumption rate of soleus muscle of SAMP8 mice. Data are presented as mean+/−SD. #$p<0.05$ versus non-aging group; *$p<0.05$ versus aging group.

Oral administration of PS23 increased the oxygen consumption rate of soleus muscle in aged SAMP8 mice (FIG. 22).

Figure 23:
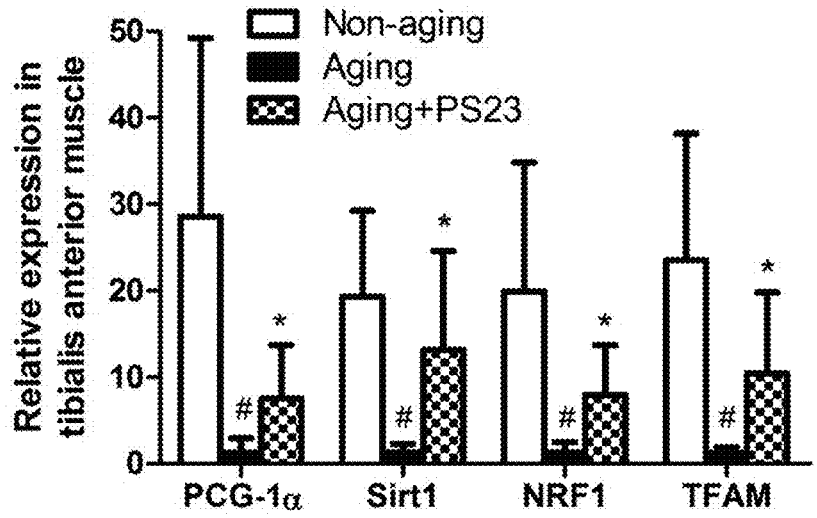
FIG. 23 shows muscle mitochondria synthesis related gene expression in tibialis anterior muscle of SAMP8 mice. Data are presented as mean+/−SD. #$p<0.05$ versus non-aging group; *$p<0.05$ versus aging group.

Oral administration of PS23 increased the muscle mitochondria synthesis related gene expression in aged SAMP8 mice (FIG. 23).

Figure 24:
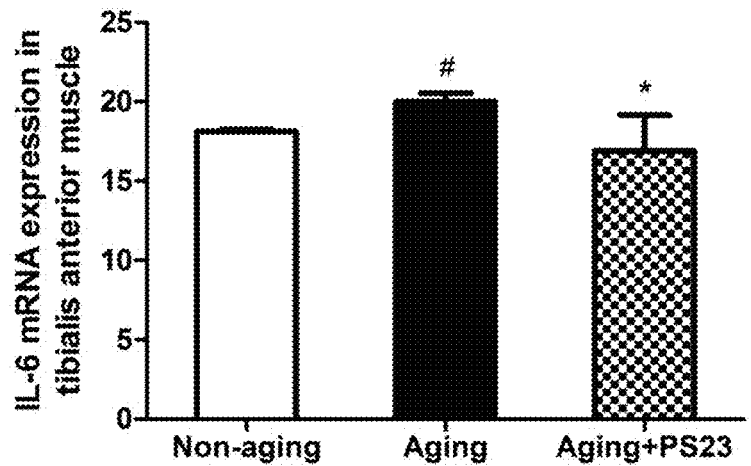
FIG. 24 shows gene expression of inflammatory cytokine IL-6 in tibialis anterior muscle of SAMP8 mice. Data are presented as mean+/−SD. #$p<0.05$ versus non-aging group; *$p<0.05$ versus aging group.

Oral administration of PS23 decreased the inflammatory cytokine IL-6 gene expression in the tibialis anterior muscle of aged SAMP8 mice (FIG. 24).

Figure 25:
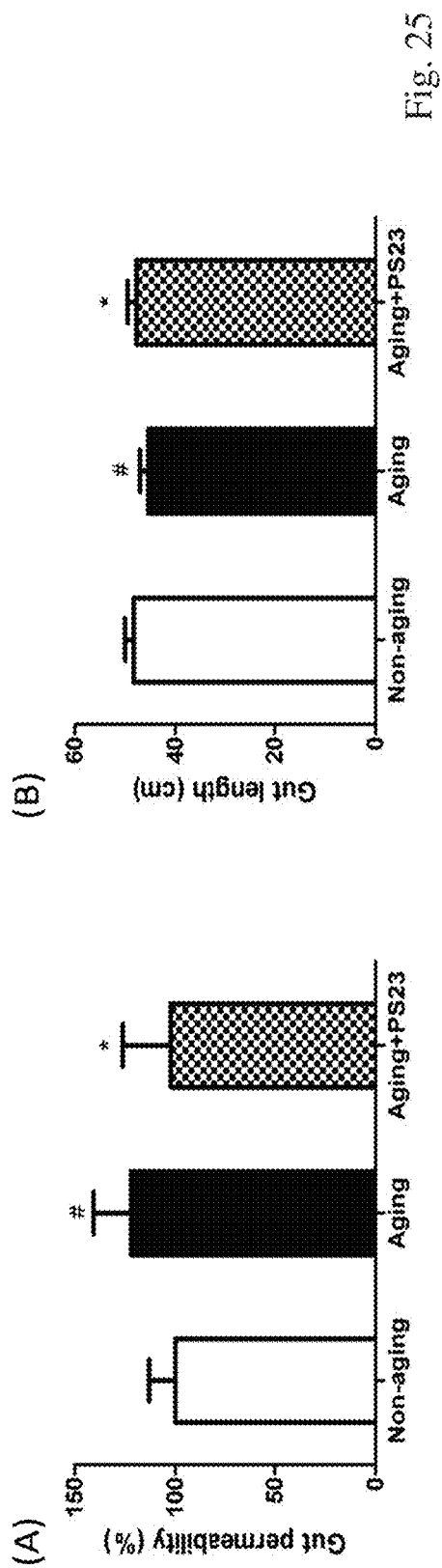
FIGS. 25 (A) and (B) show gut permeability (A) and gut length (B) of SAMP8 mice. Data are presented as mean+/−SD. #$p<0.05$ versus non-aging group; *$p<0.05$ versus aging group.

Oral administration of PS23 ameliorated the gut permeability and repaired the gut length impaired by aging process in aged SAMP8 mice (FIGS. 25 (A) and (B)).

Figure 26:
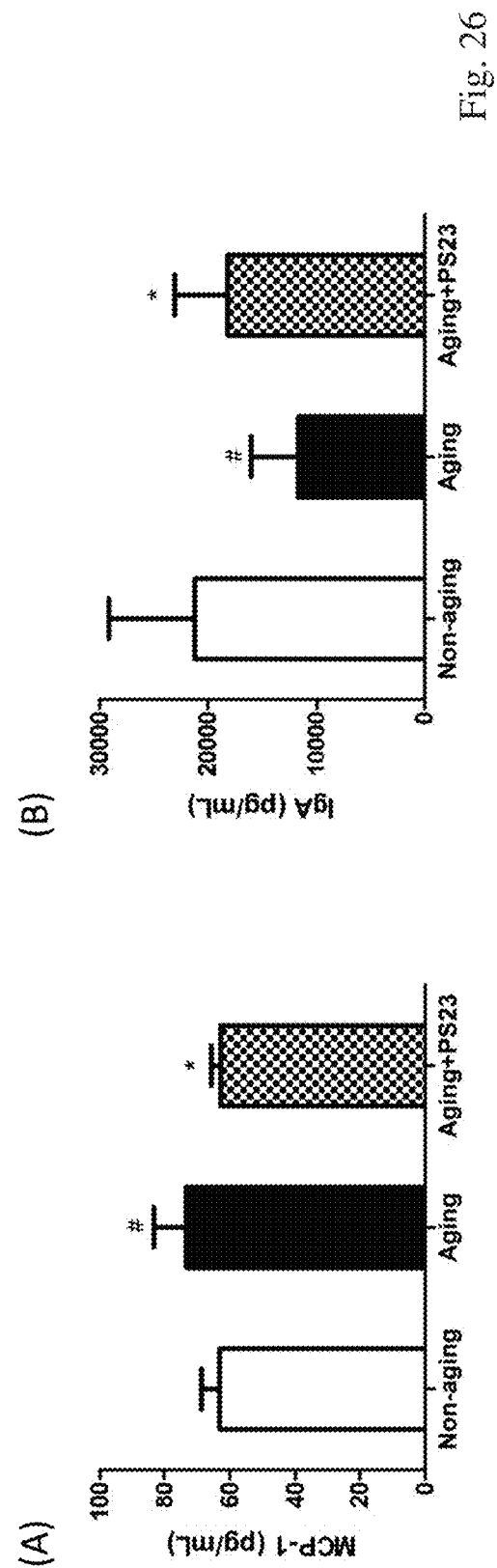
FIGS. 26 (A) and (B) show the level of MCP-1 (A) and IgA (B) in the intestinal fluid if SAMP8 mice. Data are presented as mean+/−SD. #$p<0.05$ versus non-aging group; *$p<0.05$ versus aging group.

Oral administration of PS23 decreased inflammatory chemokine MCP-1 and increased secretory IgA in the intestinal fluid of aged SAMP8 mice (FIGS. 26 (A) and (B)).

Example 10 PS23 Prevent and Treat Stress-Related Disorders

Figure 34:
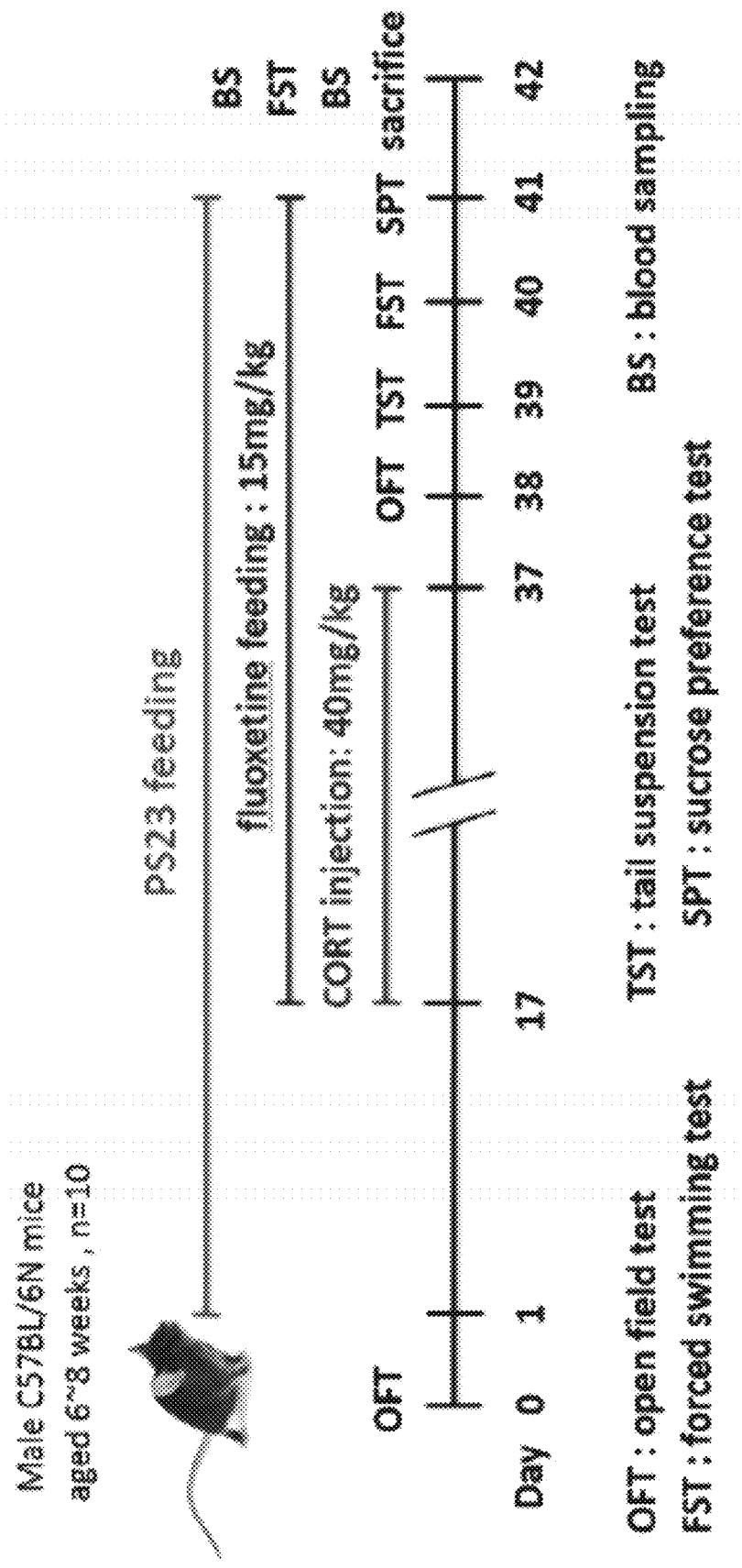
FIG. 34 shows the experimental design of depression model induced by repeated corticosterone injections.

PS23 prevent and treat stress-related disorders. The experimental design of depression model induced by repeated corticosterone injections is shown in FIG. 34.

Figure 27:
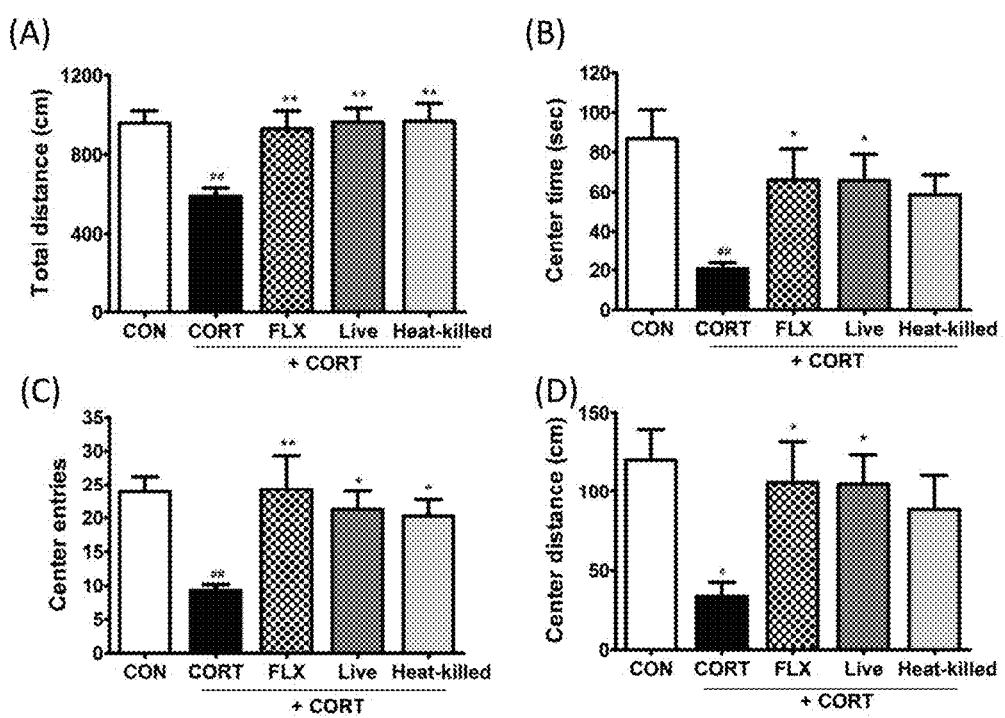
FIGS. 27 (A) to (D) show the total distance (A), center time (B), center entries (C), and center distance (D) of repeated CORT injection mice were assessed by open field test. Data are presented as mean±SD. #$p<0.05$, ##$p<0.01$ versus CON group; *$p<0.05$, **$p<0.01$ versus CORT group.

Oral administration of live or heat-killed PS23 rescued CORT-induced anxiety-like behavior and exploratory activity (FIGS. 27 (A) to (D)).

Figure 28:
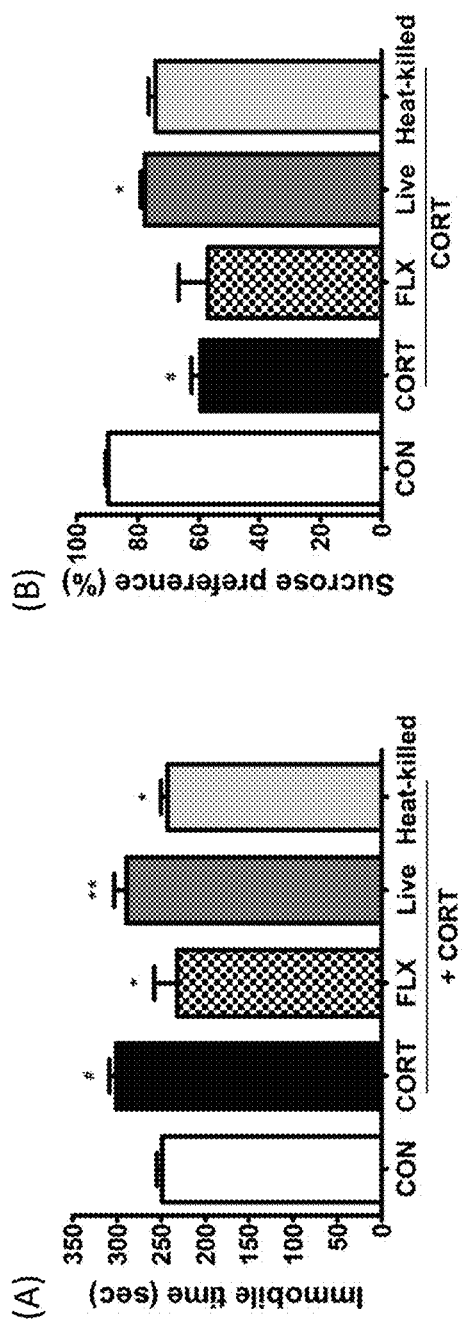
FIGS. 28 (A) and (B) show the immobile time assessed by forced swimming test (A) and sucrose preference (B) of repeated CORT injection mice. Data are presented as mean±SD. #$p<0.05$ versus CON group; *$p<0.05$, **$p<0.01$ versus CORT group.

Oral administration of live or heat-killed PS23 rescued CORT-induced depression-like behavior (FIGS. 28 (A) and (B)).

Figure 29:
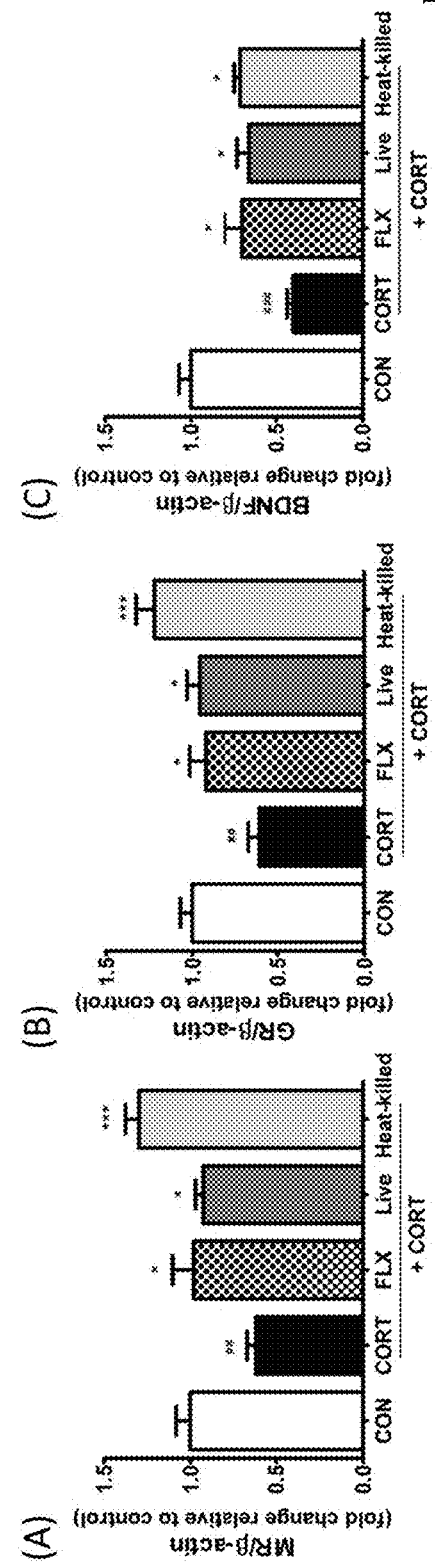
FIGS. 29 (A) to (C) show the relative expression level of mineralocorticoid receptor (A), glucocorticoid receptor (B), and BDNF (C) in the hippocampus of repeated CORT injection mice. Data are presented as mean±SD. ##$p<0.01$, ###$p<0.001$ versus CON group; *$p<0.05$, ***$p<0.001$ versus CORT group.

Oral administration of live or heat-killed PS23 increased glucocorticoid receptor (GR), mineralocorticoid receptor (MR), and BDNF protein expression in hippocampus, and protect the neurons against stress (FIGS. 29 (A) to (C)).

Figure 30:
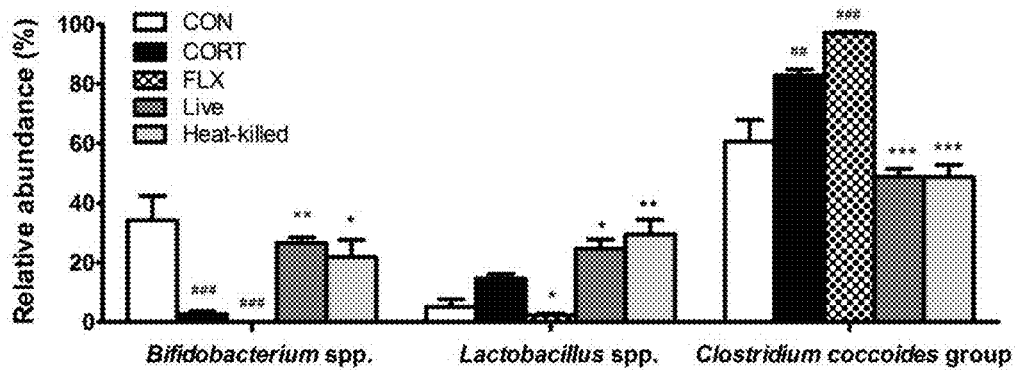
FIG. 30 shows the relative abundance of *Bifidobacterium* spp., *Lactobacillus* spp., and *Clostridium coccoides* group in the feces of repeated CORT injection mice. Data are presented as mean±SD. ##$p<0.01$, ###$p<0.001$ versus CON group; *$p<0.05$, $p<0.01$, *$p<0.001$ versus CORT group.

Oral administration of live or heat-killed PS23 increased the relative abundance of "good" bacteria like *Lactobacillus* spp. and *Bifidobacterium* spp., and decreased the relative abundance of "bad" bacteria like *Clostridium* in CORT-induced depression mice. The results showed that oral administration of PS23 may modulate the gut microbiota (FIG. 30).

Figure 31:
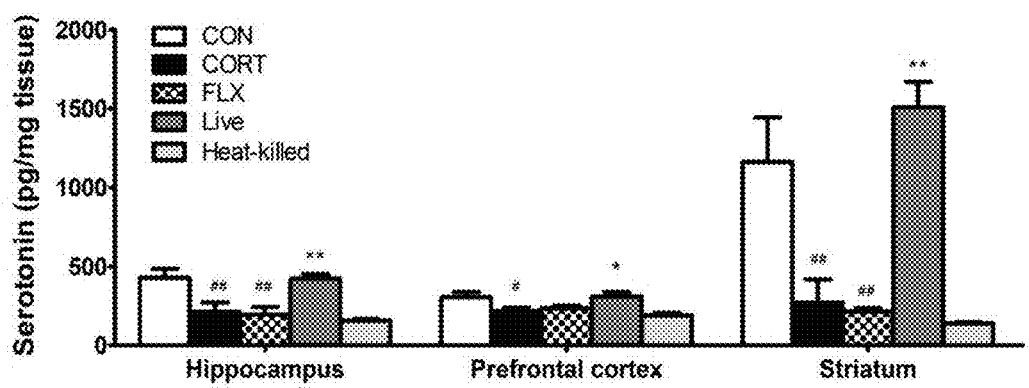
FIG. 31 shows the serotonin level in the brain tissue of repeated CORT injection mice. Data are presented as mean±SD. #$p<0.05$, ##$p<0.05$ versus CON group; *$p<0.05$, **$p<0.01$ versus CORT group.

Oral administration of PS23 increased serotonin level in the brain of CORT-induced depression mice (FIG. 31).

Figure 32:
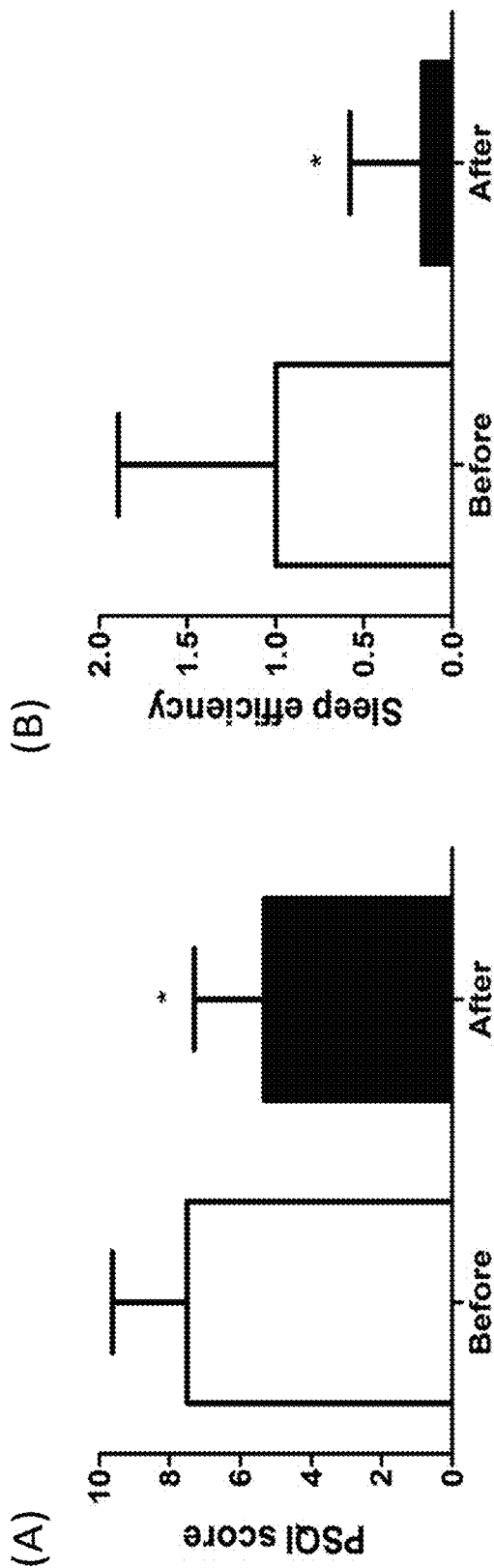
FIGS. 32 (A) and (B) show that orally administration PS23 for one week improves the PSQI score (A) and sleep efficiency (B). Data are presented as mean±SD. *$p<0.05$.

PS23 improves sleep quality and efficiency. Six healthy people orally administered PS23 ($3\times10^{10}$ CFU/day) daily for one week. Sleep quality and efficiency were assessed by Pittsburgh Sleep Quality Index (PSQI) at day 0 and day 7. The results showed that oral administration of PS23 improves sleep quality and sleep efficiency (FIGS. 32 (A) and (B)).

We claim:

1. A method for (i) treating or preventing inflammatory bowel syndrome a subject in need thereof, (ii) treating or preventing anxiety, inflammation, and/or HPA axis dysfunction in a subject suffering from maternal separation (MS) and/or (iii) treating or preventing sarcopenia in a subject in need thereof, comprising administering the isolated and purified lactic acid bacteria *Lactobacillus paracasei* PS23 (PS23), deposited with Deutsche Sammlung von Mikroorganismen und Zellkulturen under Budapest Treaty and was given the accession number DSM 32322 or a composition comprising PS23 to the subject, wherein the PS23 is administered in an amount ranging from about $1\times10^{7}$ to about $1\times10^{13}$ cells/day of heat-killed PS23 cells or about $1\times10^{7}$ to about $1\times10^{13}$ CFU/day of live PS23 cells.

2. The method of claim 1, wherein the composition comprises an edible carrier or a pharmaceutically acceptable carrier.

3. The method of claim 1, wherein the PS23 is used in a form of whole bacteria which are viable cells or dead cells.

4. The method of claim 1, wherein the composition is in a form suitable for oral administration.

5. The method of claim 1, wherein the composition is in a form of solid, semi-solid, liquid, or granule of powder.

* * * * *